United States Patent
Takahashi et al.

(10) Patent No.: US 6,548,487 B2
(45) Date of Patent: *Apr. 15, 2003

(54) AGENT FOR TREATMENT OF BLADDER TROUBLES

(75) Inventors: Katsuya Takahashi, Saitama (JP); Satoshi Miyauchi, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/778,634

(22) Filed: Feb. 7, 2001

(65) Prior Publication Data

US 2001/0044423 A1 Nov. 22, 2001

Related U.S. Application Data

(63) Continuation-in-part of application No. 09/142,032, filed as application No. PCT/JP97/04894 on Dec. 26, 1997, now Pat. No. 6,232,301.

(30) Foreign Application Priority Data

Dec. 27, 1996 (JP) .............................................. 8-351609

(51) Int. Cl.$^7$ ................................................ A61K 31/70
(52) U.S. Cl. ........................... 514/54; 514/391; 514/777
(58) Field of Search ........................... 514/54, 391, 777

(56) References Cited

U.S. PATENT DOCUMENTS

| | | | |
|---|---|---|---|
| 4,141,973 A | | 2/1979 | Balazs |
| 4,711,780 A | | 12/1987 | Fahim |
| 4,966,890 A | | 10/1990 | Gillespie |
| 5,180,715 A | | 1/1993 | Parsons |
| 5,591,724 A | * | 1/1997 | Morales et al. ................ 574/54 |
| 6,232,301 B1 | * | 5/2001 | Takahashi et al. ............. 514/54 |

FOREIGN PATENT DOCUMENTS

| | | |
|---|---|---|
| WO | WO 96/25168 | 8/1996 |
| WO | WO98/29125 | 9/1998 |

OTHER PUBLICATIONS

Philip M. Hanno, et al., "The Protective Effect of Heparin in Experimental Bladder Infection." Journal of Surgical Research 25, pp. 324–329 (1978).

C. Lowell Parsons, et al., "Antibacterial Activity of Bladder Surface Mucin Duplicated by Exogenous Glycosaminoglycan (Heparin)." Infection and Immunity, May 1979, pp. 552–557.

J. Eldrup, et al. "Permeability and Ultrastructure of Human Bladder Epithelium." British Journal of Urology, (1983) 44. pp. 488–492.

A. Morales, et al., "Intravesical Hyaluronic Acid in the Treatment of Refractory Interstitial Cystitis." *Journal of Urology*, vol. 156, Jul. 1996, pp. 45–48.

* cited by examiner

*Primary Examiner*—Elli Peselev
(74) *Attorney, Agent, or Firm*—Knobbe, Martens, Olson & Bear, LLP

(57) ABSTRACT

A method for promoting vesical mucosa epithelium dilatation and/or healing vesical mucosa of a patient's bladder, comprising: administering to the inside of the patient's bladder a solution comprising hyaluronic acid and/or a pharmaceutically acceptable salt thereof in an amount of more than 0.3 to less than 0.6% by weight until promotion of vesical mucosa epithelium dilatation and/or healing vesical mucosa is observed, and a kit comprising a solution containing more than 0.3% by weight and less than 0.6% by weight of hyaluronic acid and/or a pharmaceutically acceptable salt thereof, and a container which contains the solution and is adapted for administration of the solution to the inside of a bladder.

6 Claims, 12 Drawing Sheets

AGENT FOR TREATMENT OF BLADDER TROUBLES

CROSS-REFERENCE TO RELATED APPLICATIONS

This application is a continuation-in-part of application Ser. No. 09/142,032 filed Aug. 27, 1998, now U.S Pat. 6,232,301B 1, which is a 35 U.S.C. Section 371 application of PCT/JP97/04894, filed Dec. 26, 1997.

BACKGROUND OF THE INVENTION

The present invention relates to an agent for treatment of bladder troubles. More precisely, it relates to an agent for treatment of bladder troubles having excellent curative effect for bladder troubles exerted through action for promoting vesical mucosa epithelium dilatation or action for healing vesical mucosa.

Cystitis (bladder trouble) is caused by various kinds of causes. However, it is mostly caused by bacteria, and typical example of such cystitis is acute bacterial cystitis. Parsons, C. L. et al. have found that, when glycosaminoglycan (occasionally be abbreviated as GAG hereinafter) layer coating bladder is removed by acid treatment, bacterial adhesion to the bladder increases, and found that the amount of such adhesion of bacteria decreases when heparin, which is an exogenous GAG, is instilled into the bladder (J. Surg. Res. 25:324-329 (1978)). A later study has suggested that exogenously administered heparin should coat migrating cells on the bladder surface, and act as a barrier for the bacteria and migrating cells (Infect. Immun. 24:552-557 (1979)).

Non-bacterial intractable cystitis showing symptoms similar to those of acute bacterial cystitis but not responding to antibacterial agents has been known. Representative kinds of non-bacterial intractable cystitis are roughly classified into (1) interstitial cystitis, (2) eosinophilic cystitis, and (3) hemorrhagic cystitis. Interstitial cystitis is a disease frequently found in Europe and America, and it shows increased urinary frequency extending for ten months in middle-age or older females as main symptom and characterized by pain of suprapubic region when the bladder is filled. Interstitial cystitis causes decrease of bladder capacity, and petechia is observed in submucosal area when bladder wall expands, and there may be sometimes observed intravesical ulcer. As a pathological aspect, fibrillation of vesical mucosa is observed. As to the etiology of interstitial cystitis, there have been suggested collagen disease theory, autoimmune disease theory and the like, but it has not been fully elucidated. This disease is usually treated by instillation of dimethyl sulfoxide (DMSO), oxychlorosene sodium and the like. However, because effectiveness of these therapies can hardly be expected, vesical ectasia is eventually performed as a surgical intervention in most cases. In addition, these therapies have drawbacks, for example, the instillation of DMSO may enhance intravesical irritation sensitivity, and makes exhalation have garlic odor, and instillation of oxychlorosene sodium requires anesthesia because it is accompanied with terrible pain.

While the etiology of interstitial cystitis has not been fully elucidated as described above, it has been suggested that its major cause might be aberration or defect of glycosaminoglycan coating the transitional epithelium of bladder (Eldrup J. 1983. British J. of Urology, 55:488). As one of analogues of glycosaminoglycan, sodium pentosanpolysulfate has been known, which has low molecular weight and low viscosity, and highly charged negatively. It has been suggested that interstitial cystitis may be treated by using the pentosanpolysulfate together with a steroid for oral administration or instillation into bladder, thereby preventing intravesical angiogenesis, leakage of cell membranes and leakage and exchange of blood capillaries (U.S. Pat. Nos. 4,820,693 and 4,966,890). It has also been disclosed that the pentosanpolysulfate can inhibit adhesion of bacteria to transitional epithelium of bladder. Based on this, it has been proposed that interstitial cystitis may be treated by oral administration of the pentosanpolysulfate in a dose of 100 mg/day or more (U.S. Pat. No. 5,180,715), and it is used as an agent for oral administration (trade name: Elmiron). This patent describes that interstitial cystitis or bacterial cystitis can be treated by administering pentosanpolysulfates to patents' bladders by irrigation, while it does not disclose specific experiments of such treatment.

Eosinophilic cystitis shows exactly the same symptoms as acute bacterial cystitis, and pyuria is a typical symptom of this disease. However, antibacterial agents are not effective to this disease, and the main component of pyuria is acidophils. This pathology is an allergic reaction to an agent having anti-allergic action such as tranilast. While eosinophilic cystitis is usually ameliorated by withdrawing administration of the causative agent, a steroid is effective when it is not readily ameliorated. When the steroid is not effective, bladder enucleation might be unavoidable. Hemorrhagic cystitis is an affection accompanied by severe hematuria as the chief complaint, and as hemorrhagic cystitis there have been known, for example, radiation cystitis, which is observed in radiotherapy of uterine cancer, rectal cancer, bladder cancer and the like, and which makes vesical mucosa hemorrhagic labile, and is accompanied by hematuria; and drug cystitis, whose typical example is one causing uncontrollable cystorrhagia when treating malignancies with chemotherapeutants such as cyclophosphamide.

For the treatment of radiation cystitis, intravesical electrocauterization or intravesical perfusion of aluminum potassium sulfate is effective for those in mild condition, whereas bladder enucleation or ectasia is used for severe cases. On the other hand, electrocauterization and intravesical perfusion of aluminum potassium sulfate are not effective for the drug cystitis, and intravesical instillation of formalin is used for its emergent cases. Bladders may shrink after the formalin instillation, and bladder ectasia is used for such cases.

As described above, any suitable therapies for non-bacterial intractable cystitis, in particular, for interstitial cystitis and hemorrhagic cystitis have not been developed yet. It has been known to use heparin, which is a GAG, or a pentosanpolysulfate, which is a synthesized analog of GAG, for the treatment of bacterial cystitis and interstitial cystitis. However, because the former has an average molecular weight of around 10,000, and the latter has a molecular weight of around 1,600–60,000 and they exhibit low viscosity, they can exhibit only poor activity for coating the highly viscous GAG layer in bladders. In addition, because they have a lot of sulfate groups in their molecules and hence exhibit strong anti-thrombogenic action, namely, hemorrhagic action, care must be taken for bleeding from mucosa when they are used for the treatment of bacterial cystitis and interstitial cystitis, and they cannot be used for the treatment of hemorrhagic cystitis.

It has recently been reported that symptoms of interstitial cystitis were ameliorated by vesical instillation of aqueous solution of sodium hyaluronate (Proceedings of The American Urological Association, Vol.153, April 1995 supplement; WO96/25168. In this report, the symptom amelioration effect mentioned above was specifically confirmed only for the case where a solution formed by dissolving 40 mg of the hyaluronate in 50 ml of physiological saline (0.08% solution). However, according to the present inventors' supplementary examination, it was found that 0.08% hyaluronate solution could not prevent progress of fibrillation of bladders.

There has never been reported that hyaluronic acid and salts thereof have action for promoting vesical mucosa epithelium dilatation or action for healing vesical mucosa. There has also never been reported that a hyaluronic acid solution prevents fibrillation of bladder in non-bacterial intractable cystitis, or heals damaged vesical mucosa. Furthermore, effective concentration of the hyaluronic acid solution, molecular weight of hyaluronic acid, and other parameters for obtaining such actions as mentioned above have never been specifically examined.

SUMMARY OF THE INVENTION

The present invention has been completed under the circumstances described above, and its object is to provide an agent for treatment of bladder troubles that has vesical mucosa epithelium dilatation promoting action and/or vesical mucosa healing action, and exhibits excellent curative effect for bladder troubles, in particular, non-bacterial intractable bladder troubles.

The present inventors conducted various studies in order to achieve the above object, and as a result they found that, in the treatment of bladder troubles, the bladder troubles can be effectively treated by administering a solution of hyaluronic acid and/or a pharmaceutically acceptable salt thereof at a specific concentration directly into bladder, thereby promoting dilatation of vesical mucosa epithelium or healing vesical mucosa. The present invention has been completed on the basis of these findings.

The present invention provides a method for promoting vesical mucosa epithelium dilatation and/or healing vesical mucosa of a patient's bladder, comprising: administering to the inside of the patient's bladder a solution comprising hyaluronic acid and/or a pharmaceutically acceptable salt thereof in an amount of more than 0.3 to less than 0.6% by weight until promotion of vesical mucosa epithelium dilatation and/or healing vesical mucosa is observed.

The present invention also provide a kit comprising a solution containing more than 0.3% by weight and less than 0.6% by weight of hyaluronic acid and/or a pharmaceutically acceptable salt thereof, and a container which contains the solution and is adapted for administration of the solution to the inside of a bladder.

DETAILED DESCRIPTION OF THE INVENTION

Figure 1:
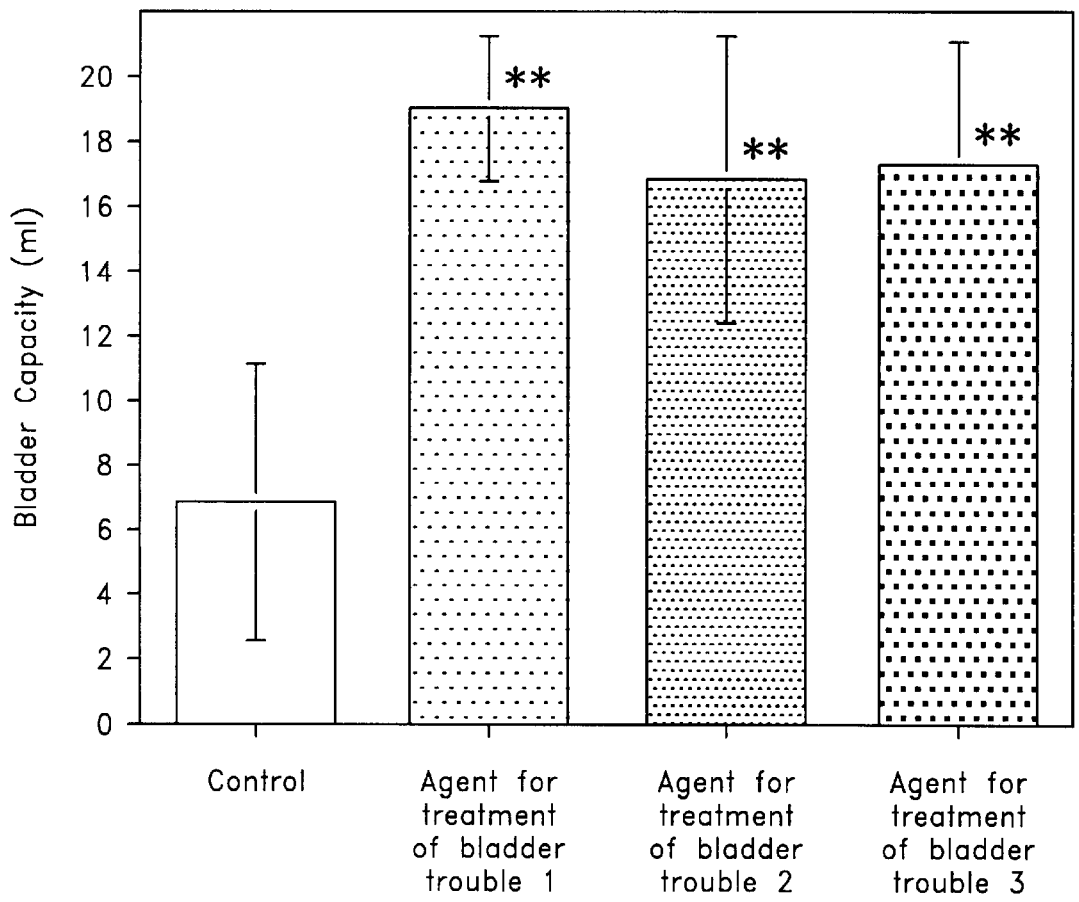
FIG. 1 is a graph representing bladder capacity in 5% acetic acid-induced rabbit cystitis models for control and groups administered with agents for treatment of bladder troubles.
Figure 2:
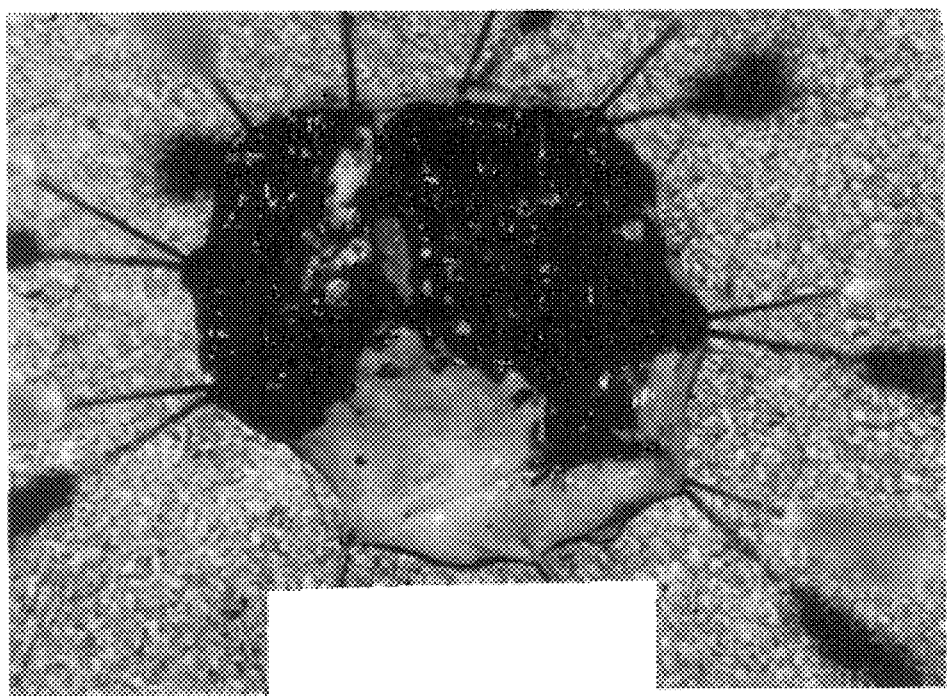
FIG. 2 is a representative photograph of dissected bladder showing trypan blue adhesion to vesical mucosa in a 5% acetic acid-induced rabbit cystitis model for control.
Figure 3:
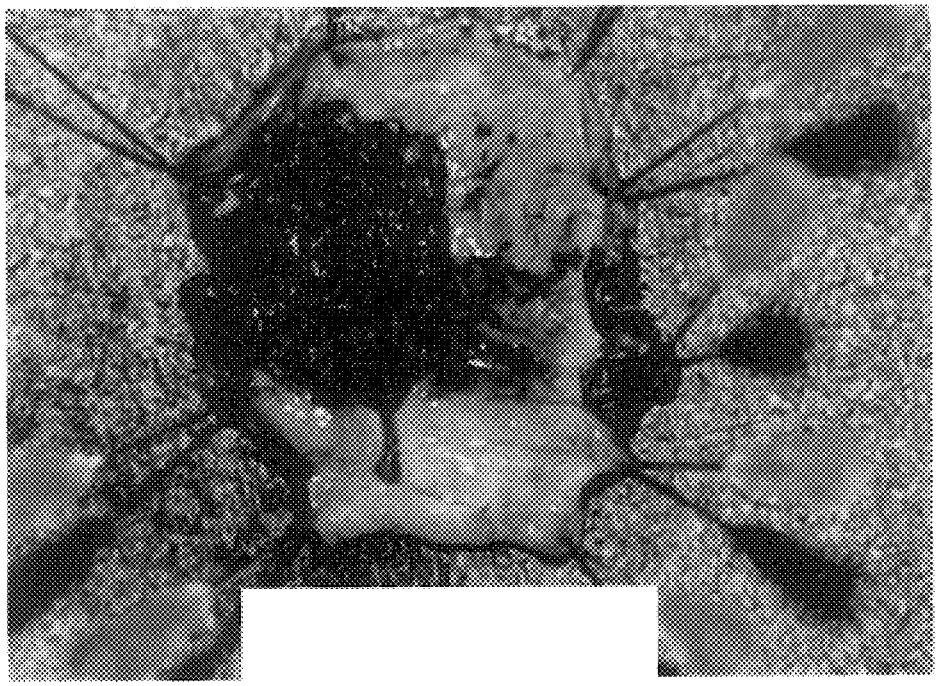
FIG. 3 is a representative photograph of dissected bladder showing trypan blue adhesion to vesical mucosa in a 5% acetic acid-induced rabbit cystitis model for a group administered with agent for treatment of bladder troubles 1.
Figure 4:
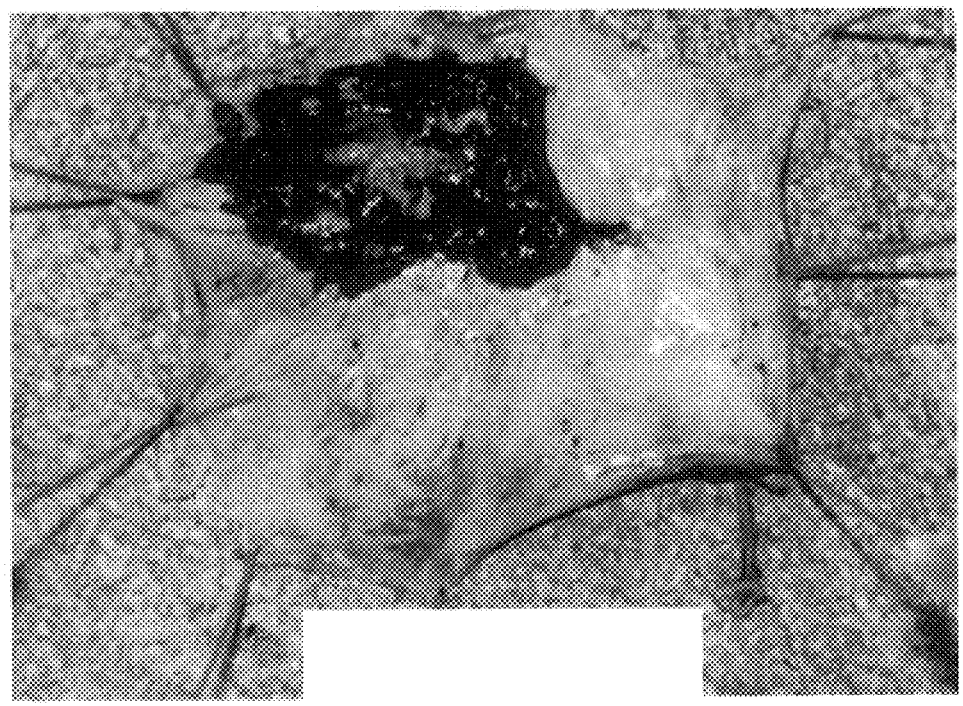
FIG. 4 is a representative photograph of dissected bladder showing trypan blue adhesion to vesical mucosa in a 5% acetic acid-induced rabbit cystitis model for a group administered with agent for treatment of bladder troubles 2.
Figure 5:
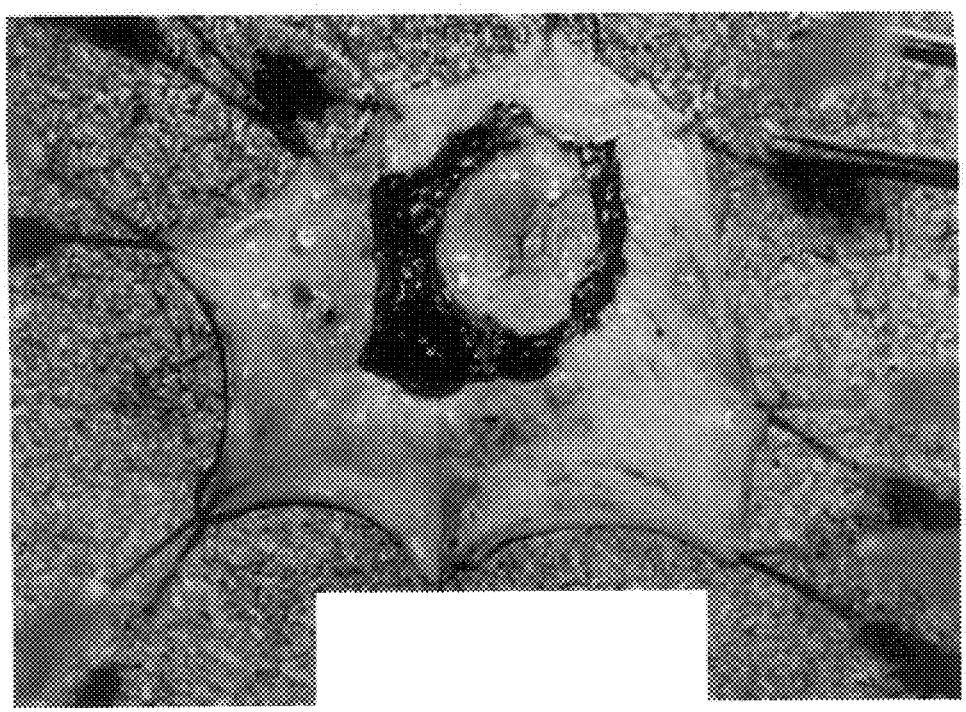
FIG. 5 is a representative photograph of dissected bladder showing trypan blue adhesion to vesical mucosa in a 5% acetic acid-induced rabbit cystitis model for a group administered with agent for treatment of bladder troubles 3.

The present invention will be explained in detail hereinafter. The solution of hyaluronic acid and/or a pharmaceutically acceptable salt thereof used in the method and the kit of the present invention is also herein referred to as the agent for treatment of bladder troubles of the present invention.

Hyaluronic acid and/or pharmaceutically acceptable salts thereof contained in the solution constituting the agent for treatment of bladder troubles of the present invention will be explained first.

(1) Hyaluronic Acid and/or Pharmaceutically Acceptable Salts Thereof

Hyaluronic acid and/or pharmaceutically acceptable salts thereof used for the agent for treatment of bladder troubles of the present invention are not particularly limited, so long as they can effectively treat bladder troubles when used as a solution of a certain concentration. As the hyaluronic acid and/or pharmaceutically acceptable salts thereof used for the agent for treatment of bladder troubles of the present invention, hyaluronic acid and/or a pharmaceutically acceptable salt thereof having action for promoting vesical mucosa epithelium dilatation and/or action for healing vesical mucosa are particularly preferred.

As the hyaluronic acid and/or pharmaceutically acceptable salts thereof used for the agent for treatment of bladder troubles of the present invention, hyaluronic acid and/or pharmaceutically acceptable salts thereof having the following physicochemical properties can be specifically mentioned:

(A) endotoxin content; 0.03 EU (endotoxin unit)/10 mg or less,
(B) sulfur content; 0.01% or less as determined by coulometric titration,
(C) iron content; 20 ppm or less,
(D) protein content; 0.1% or less, and
(E) weight average molecular weight; 500,000 or more.

The properties (A) to (E) mentioned above are determined by methods commonly used by those skilled in the art for determining such physicochemical properties.

Specific examples of the hyaluronic acid and/or pharmaceutically acceptable salts thereof used for the agent for treatment of bladder troubles of the present invention include, for example, those having the aforementioned properties (A) to (D) and having a weight average molecular weight of around 500,000–4,000,000, preferably around 500,000–2,200,000, more preferably around 600,000–1,200,000 or 500,000–1,100,000, particularly preferably 800,000–1,200,000 or 700,000–1,100,000. If concentration and viscosity of the solution are selected adequately, hyaluronic acid and/or pharmaceutically acceptable salts thereof having a weight average molecular weight of around 1,500,000–2,200,000 or around 1,900,000–3,900,000 can also be used.

As the hyaluronic acid and/or pharmaceutically acceptable salts thereof used for the agent for treatment of bladder troubles of the present invention, hyaluronic acid and/or pharmaceutically acceptable salts thereof having the aforementioned physicochemical properties (A) to (E) and having a limiting viscosity of 11.0–45 (dl/g) can also be mentioned.

As for the agent for treatment of bladder troubles of the present invention, if hyaluronic acid and/or pharmaceutically acceptable salts thereof having an endotoxin content; sulfated glycosaminoglycan content, iron content; protein content; weight average molecular weight; and/or limiting viscosity outside the above-defined ranges are used, it may cause exacerbation of inflammation and hemorrhage, allergic reactions and the like, or the desired effect may not be obtained.

As the pharmaceutically acceptable salts of hyaluronic acid used for the agent for treatment of bladder troubles of the present invention, pharmaceutically acceptable water-soluble metal salts of hyaluronic acid such as sodium hyaluronate, potassium hyaluronate, and calcium hyaluronate are usually used. Among these, sodium hyaluronate, which is used mainly for medical purposes including medicaments, medical devices and the like, is preferred. Origin of hyaluronic acid and/or pharmaceutically acceptable salts thereof, and production method therefor are not particularly limited. For example, they can be produced from chicken crest, animal umbilical cord, skin, vitreous body or the like by extraction using any optional combination of heat treatment, organic solvent treatment, mincing, protease treatment and the like, and purification using any optional combination of salting out with ammonium sulfate, precipitation with organic solvents such as ethanol, fractional precipitation with quaternary ammonium salts, deproteination, absorption of impurities with absorbents (Celite, activated carbon etc.), ultrafiltration, membrane filtration and the like (see, Japanese Published Examined Patent Application Nos. 61-8083, 61-60081, 61-21241, 6-8323, U.S. Pat. Nos. 4,141,973, 5,449,104 etc.). They can also be produced by fermentation technique using microorganisms such as hemolytic streptococcus (genus Streptococcus) (see, U.S. Pat. Nos. 4,946,780, 4,780,414 etc.).

Some of such hyaluronic acid and/or pharmaceutically acceptable salts thereof are commercially available, and hence those made as preparations for medical use such as for medicaments, whose concentration of hyaluronic acid and/or pharmaceutically acceptable salts thereof and the like are adjusted depending on the purpose, can be selected from them and used for the agent for treatment of bladder troubles of the present invention. Preferred examples of such commercially available hyaluronic acid and/or pharmaceutically acceptable salts thereof include, as sodium hyaluronate satisfying the above properties (A) to (D), ARTZ (weight average molecular weight; 600,000–1,200,000), OPEGAN (weight average molecular weight; 600,000–1,200,000), and OPEGAN Hi (weight average molecular weight; 1,900,000–3,900,000) produced by SEIKAGAKU CORPORATION, Hyalein (weight average molecular weight; 600,000–1,200,000) produced by Santen Pharmaceutical Co., Ltd., OPELEAD (weight average molecular weight; 1,530,000-2,130,000) produced by Shiseido Co., Ltd., Healon (weight average molecular weight; 1,900,000–3,900,000) produced by Kabi Pharmacia Inc. and the like.

(2) Agent for Treatment of Bladder Troubles of the Present Invention

The agent for treatment of bladder troubles of the present invention comprises a solution containing hyaluronic acid and/or a pharmaceutically acceptable salt thereof in an amount effective for promoting vesical mucosa epithelium dilatation and/or healing vesical mucosa. The term amount effective for promoting vesical mucosa epithelium dilatation and/or healing vesical mucosa of hyaluronic acid and/or a pharmaceutically acceptable salt thereof contained in the solution constituting the agent for treatment of bladder troubles of the present invention means an amount sufficient for the solution to act on vesical mucosa epithelium and promote its dilatation, and/or act on vesical mucosa and heal it or reproduce it as an agent for treatment of bladder troubles. Specifically, while it depends on the kinds of hyaluronic acid and/or pharmaceutically acceptable salts thereof contained in the solution, the concentration of hyaluronic acid and/or pharmaceutically acceptable salts thereof in the solution is, for example, more than 0.3 to less than 0.6% by weight, preferably around 0.35 to less than 0.6% by weight, more preferably around 0.35 to around 0.45% by weight, particularly preferably around 0.35 to around 0.4% by weight.

It is particularly preferable that the agent of the present invention comprises hyaluronic acid and/or pharmaceutically acceptable salts thereof having a weight average molecular weight of around 500,000–1,100,000 in a concentration within the above-mentioned range.

As for the agent for treatment of bladder troubles of the present invention, when the content of hyaluronic acid and/or a pharmaceutically acceptable salt thereof in the solution is less than 0.2%, the agent may not be effectively used as the agent for treatment of bladder troubles of the present invention, because, for example, the action for promoting vesical mucosa epithelium dilatation becomes insufficient. When the content exceeds 0.6% by weight, difficulty of urination may be caused because of high viscosity.

Upon administration of the agent at an effective dose within the range defined above, vesical mucosa epithelium dilatation is promoted and the mucosa is healed and reproduced at damaged or excoriated regions of vesical mucosa epithelium caused by bladder troubles.

In non-bacterial intractable bladder troubles, patients suffer from pain when bladder is filled because nerve is usually denuded due to excoriation of vesical mucosa epithelium, and patients suffer from increased urinary frequency because of decreased bladder capacity caused by fibrillation of bladders. The agent for treatment of bladder troubles of the present invention can indirectly ameliorate such pain and prevent progress of vesical fibrillation through the aforementioned actions.

The solution containing hyaluronic acid and/or a pharmaceutically acceptable salt thereof that constitutes the agent for treatment of bladder troubles of the present invention preferably have a pH value of about 6–8, and a relative osmotic pressure to body fluid is around 0.9–1.2 (substantially isotonic as to body fluid or physiological saline).

By adjusting the pH of the solution in the agent for treatment of bladder troubles of the present invention to the aforementioned range of around 6–8, its acrimony for vesical mucosa made sensitive can be reduced. When the pH is less than 6, acrimony for vesical mucosa may become too strong. When the pH is more than 8, acrimony for vesical mucosa may become too strong, healing and reproduction of vesical mucosa may be retarded, and the preventive effect for the vesical fibrillation may be invalidated.

By adjusting the relative osmotic pressure of the solution in the agent for treatment of bladder troubles of the present invention to the aforementioned range of around 0.9–1.2, its acrimony for vesical mucosa can be reduced as in the adjustment of pH. When the relative osmotic pressure is less than 0.9, difficulty of urination may be caused by increased viscosity. When the relative osmotic pressure is more than 1.2, acrimony for vesical mucosa may become too strong.

For the agent for treatment of bladder troubles of the present invention comprising a solution containing hyaluronic acid and/or a pharmaceutically acceptable salt thereof, the solution containing hyaluronic acid and/or a pharmaceutically acceptable salt thereof is preferably an aqueous solution having an apparent viscosity of 10–1500 mPa·s as determined at a shear rate of 9.6 $sec^{-1}$ at 20° C.

By adjusting the apparent viscosity of the aqueous solution constituting the agent for treatment of bladder troubles of the present invention to around 10–1500 mPa·s, it becomes possible to obtain appropriate degree of the effect for healing vesical mucosa without causing difficulty of urination. When the apparent viscosity of the aqueous solution is less than 10 mPa·s, the effect for healing vesical mucosa may become insufficient. When the apparent viscosity of the aqueous solution exceeds 1500 mPa·s, difficulty of urination may be caused.

The present inventors found that administration of 5% acetic acid to bladders of experimental animals excoriates vesical mucosa epithelium and irreversibly promotes fibrillation of the bladders, and as a result, the bladder capacity is lowered, and that the symptoms of such animals as treated as mentioned above are quite similar to those of non-infectious intractable bladder troubles of humans. Moreover, they also found that, using the aforementioned animal models, medicaments effective for treatment of non-infectious intractable bladder troubles can be screened by evaluating the following parameters: (a) bladder capacity, (b) bladder dry weight or amount of intravesical hydroxyproline (amount of collagen), and (c) amount of intravesical trypan blue adhesion or area of trypan blue adhesion to the excoriation region of vesical mucosa, which reflect (A) degree of vesical expansion, (B) degree of fibrillation of bladder proper muscle coat, and (C) degree of dilatation of vesical mucosa epithelium and/or degree of healing of vesical mucosa, respectively.

The term "5% acetic acid" herein used refers to a solution containing acetic acid at a concentration of 5%.

Specific examples of the solution containing hyaluronic acid and/or a pharmaceutically acceptable salt thereof, which constitutes the agent for treatment of bladder troubles of the present invention, include such a solution prepared so that bladder capacity of a rabbit which has been subjected to vesical mucosa excoriation treatment by introducing 5% acetic acid into bladder and retaining it for 10 minutes, and then a treatment by introducing the solution to the bladder every day for seven days after the excoriation of the vesical mucosa should be 2 to 3 times as large as bladder capacity of a rabbit which has been subjected to the same vesical mucosa excoriation treatment with 5% acetic acid as mentioned above and a treatment by introducing phosphate buffered physiological saline instead of the solution in the same manner; such a solution prepared so that bladder dry weight of a rabbit which has been subjected to the same vesical mucosa excoriation treatment with 5% acetic acid as mentioned above and then the same treatment by introducing the solution as mentioned above should be 0.6 to 0.9 times as large as bladder dry weight of a rabbit which has been subjected to the same vesical mucosa excoriation treatment with 5% acetic acid as mentioned above and the same treatment by introducing phosphate buffered physiological saline instead of the solution as mentioned above; and the like.

Specific examples of the solution containing hyaluronic acid and/or a pharmaceutically acceptable salt thereof, which constitutes the agent for treatment of bladder troubles of the present invention, further include such a solution prepared so that amount of intravesical trypan blue adhesion of a rabbit which has been subjected to vesical mucosa excoriation treatment by introducing 5% acetic acid to bladder and retaining it for 10 minutes, then a treatment by introducing the solution to the bladder every day for seven days after the excoriation of the vesical mucosa, and then a treatment by introducing 0.5% aqueous trypan blue solution to the bladder to obtain trypan blue adhesion should be 0.5 to 0.7 times as large as amount of intravesical trypan blue adhesion of a rabbit which has been subjected to the same vesical mucosa excoriation treatment with 5% acetic acid as mentioned above, then a treatment by introducing phosphate buffered saline instead of the solution in the same manner, and then the same trypan blue adhesion treatment as mentioned above; such a solution prepared so that trypan blue adhesion area in vesical mucosa excoriation region of a rabbit which has been subjected to the same vesical mucosa excoriation treatment with 5% acetic acid as mentioned above, then the same treatment with the solution as mentioned above, and then the same trypan blue adhesion treatment as mentioned above should be 0.25 to 0.45 times as large as trypan blue adhesion area in vesical mucosa excoriation region of a rabbit which has been subjected to the same vesical mucosa excoriation treatment with 5% acetic acid as mentioned above, then a treatment by introducing phosphate buffered saline instead of the solution in the same manner, and then the same trypan blue adhesion treatment as mentioned above; and the like.

Specific examples of the solution containing hyaluronic acid and/or a pharmaceutically acceptable salt thereof further include such a solution prepared so that amount of intravesical hydroxyproline of a rabbit which has been subjected to the same vesical mucosa excoriation treatment with 5% acetic acid as mentioned above, and then the same treatment with the solution as mentioned above should be 0.8 to 0.9 times as large as amount of intravesical hydroxyproline of a rabbit which has been subjected to the same vesical mucosa excoriation treatment with 5% acetic acid as mentioned above, and then a treatment by introducing phosphate buffered saline instead of the solution in the same manner; and the like.

The solution containing hyaluronic acid and/or a pharmaceutically acceptable salt thereof, which constitutes the agent for treatment of bladder troubles of the present invention, such as those specifically mentioned above, is a solution selected based on evaluation of the action for promoting vesical mucosa epithelium dilatation and/or action for healing vesical mucosa of the solution in bladders of rabbits whose vesical mucosa has been excoriated by introducing 5% acetic acid into their bladders and retaining it for 10 minutes as a model, more specifically, selected based on the following indexes, action for increasing bladder capacity, action for decreasing bladder dry weight, action for decreasing amount of intravesical trypan blue adhesion or trypan blue adhesion area at vesical mucosa excoriated region, action for decreasing amount of intravesical hydroxyproline and the like of the solution, which indexes are determined by comparing results obtained in the model when the solution is used and result obtained when phosphate buffered saline is used in the same manner instead of the solution. These indexes will be explained hereinafter.

The rabbit model whose vesical mucosa is excoriated, referred to as rabbit vesical mucosa trouble model hereinafter, will be explained first. It has been known that acetic acid has mucosa acrimony, and gastric mucosa trouble models prepared by using acetic acid have widely been used for tests of medicaments and the like. Therefore, in the present invention, a rabbit vesical mucosa trouble model was created in which vesical mucosa is excoriated by applying acetic acid to the vesical mucosa as described above, and factors representing the action for promoting vesical mucosa epithelium dilatation and/or the action for healing vesical mucosa measured in this model were used as indexes for selecting solutions constituting the agent for treatment of bladder troubles of the present invention as described above.

The rabbit vesical mucosa trouble model is prepared, for example, as follows. A bladder catheter is inserted into bladder of rabbit under general anesthesia obtained by a usual method, and then residual urine in the bladder is drained using an infusion pipe of a suitable size. After the drainage of residual urine, the inside of the bladder is washed with sufficient amount of physiological saline. Then, a solution comprising acetic acid diluted with distilled water to a concentration of 5% is introduced into the bladder in an amount sufficiently filling the bladder, and retained for 10 minutes so that vesical mucosa should be excoriated. Subsequently, the acetic acid is drained, and intravesical irrigation is performed with a sufficient amount of physiological saline.

In the present invention, while the rabbit vesical mucosa trouble model treated with 5% acetic acid for ten minutes is used as the standard, any similar models may be used for evaluation tests of various drug substances. In such cases, acetic acid concentration of the acetic acid solution used for excoriation of vesical mucosa is not limited to 5%, and retention time of the acetic acid solution in bladder is not limited to ten minutes. These factors may be appropriately modified as required according to the circumferential conditions. Though kind, age represented by week-basis, and sexuality of rabbits used for the model production are not particularly limited, preferred example of the rabbits include JW male rabbits of 12–14 week old and the like. Animals other than rabbit can also be used.

The factors for evaluating action for promoting vesical mucosa epithelium dilatation and/or action for healing vesical mucosa upon applying the pharmaceutical solution to bladder of the aforementioned vesical mucosa trouble model will be explained hereinafter.

If the bladder treated with acetic acid as described above is not given any appropriate therapeutic treatment, severe inflammation should be induced after the excoriation of vesical mucosa epithelium, and fibrillation of vesical proper muscle coat should be caused after a few days, which makes bladder expansion very difficult. In contrast, if any effective curative treatment is given, dilatation of vesical mucosa epithelium should be promoted, and fibrillation of vesical proper muscle coat should be prevented because of healing of vesical mucosa, thereby the expansion function of bladder should be improved.

Therefore, degree of expansion function of bladder can be evaluated by measuring bladder capacity. In other words, the larger the bladder capacity of the aforementioned rabbit vesical mucosa trouble model after the bladder of the model is applied with a solution of various agents, the more the bladder function is recovered. Further, degree of fibrillation of vesical proper muscle coat can be evaluated by measuring bladder dry weight and intravesical amount of hydroxyproline (collagen). That is, the larger the bladder dry weight or the smaller the intravesical amount of hydroxyproline of the aforementioned rabbit vesical mucosa trouble model after the bladder of the model is applied with a solution of various agents, the stronger the ability of preventing fibrillation of vesical proper muscle coat of the solution.

Furthermore, because it has been known that trypan blue, an acidic living tissue staining agent, can stain damaged mucosa well, degree of dilatation of vesical mucosa epithelium or degree of healing of vesical mucosa can be evaluated by measuring amount of intravesical trypan blue adhesion or trypan blue adhesion area at excoriation region of vesical mucosa. That is, the smaller the amount of intravesical trypan blue adhesion, or the trypan blue adhesion area at excoriation region of vesical mucosa after the bladder of the model is applied with a solution of various agents, the more the solution can promote dilatation of vesical mucosa epithelium or healing of vesical mucosa.

In the present invention, results obtained by daily irrigation of a solution containing hyaluronic acid and/or a pharmaceutically acceptable salt thereof for 7 days to a bladder of the aforementioned rabbit vesical mucosa trouble model and results obtained by daily irrigation of phosphate buffered saline (PBS) to the same for 7 days are compared, and solutions of hyaluronic acid and/or a pharmaceutically acceptable salt thereof resulting a bladder capacity within 2 to 3 times of that obtained with PBS, bladder dry weight within 0.6–0.9 times of that obtained with PBS, amount of intravesical trypan blue adhesion within 0.5–0.7 times of that obtained with PBS, trypan blue adhesion area at vesical mucosa excoriation region within 0.25–0.45 times of that obtained with PBS, and/or amount of intravesical hydroxyproline within 0.8–0.9 times of that obtained with PBS are selected as a preferred solution for the agent for treatment of bladder troubles of the present invention.

Those solutions of hyaluronic acid and/or a pharmaceutically acceptable salt thereof not resulting, when those solutions of hyaluronic acid and/or a pharmaceutically acceptable salt thereof are administered to bladder of the aforementioned vesical mucosa trouble model, a bladder capacity within 2 to 3 times of that obtained with PBS, bladder dry weight within 0.6–0.9 times of that obtained with PBS, amount of intravesical trypan blue adhesion within 0.5–0.7 times of that obtained with PBS, trypan blue adhesion area at vesical mucosa excoriation region within 0.25–0.45 times of that obtained with PBS, and/or amount of intravesical hydroxyproline within 0.8–0.9 times of that obtained with PBS may not be effectively used as the agent for treatment of bladder troubles of the present invention. Therefore, solutions resulting the values of the evaluation factors within the ranges defined above are preferred for the agent for treatment of bladder troubles of the present invention.

The agent for treatment of bladder troubles of the present invention can be produced by dissolving hyaluronic acid and/or a pharmaceutically acceptable salt thereof in a suitable solvent so that a content within the aforementioned range can be obtained. Examples of the solvent include water, buffers, physiological saline, water containing a water-soluble organic solvent such as dimethyl sulfoxide and the like. In the present invention, water or physiological saline is preferably used. The agent for treatment of bladder troubles of the present invention may also be provided as powder of hyaluronic acid and/or a pharmaceutically acceptable salt thereof or the like, so that it can be prepared upon use into a solution having a concentration, apparent viscosity, pH, relative osmotic pressure and the like within the ranges defined above.

The agent for treatment of bladder troubles of the present invention may contain, in addition to the above-explained hyaluronic acid and/or a pharmaceutically acceptable salt thereof and a solvent, optional ingredients as required. Examples of the optional ingredients include, for example, pharmaceutically acceptable known antiinflammatory agents, analgesics, vitamins, antibacterial agents, growth factors, adhesion factors, buffers, stabilizers, inorganic salts and the like. Because the concentration of hyaluronic acid and/or a salt thereof in the solution is relatively low (e.g., 0.1–0.8% by weight, preferably 0.2–0.6% by weight), the hyaluronic acid and the like may be degraded into lower molecular weight compounds when they are subjected to heat sterilization or stored for a long term. In such a case, it is necessary to use a means for preventing the degradation of hyaluronic acid and the like into lower molecular weight compounds, which may be a known one. Examples of such means include, for example, lowering metal ion (e.g., iron ions) content in hyaluronic acid and or salts thereof to be used to 20 ppm or less, preferably 10 ppm or less (see, U.S. Pat. No. 5,559,104), adding known stabilizers capable of preventing the degradation of hyaluronic acid and the like such as citric acid, citric acid salts, and glycerin (see, Japanese Patent Application Laid-open Nos. 8-104642 and 9-176020) and the like.

The agent for treatment of bladder troubles of the present invention is an agent to be directly administered to bladders, and it can be administered by a method usually used for medicaments usually administered directly to bladders. For example, administration method using a intravesical catheter may be used.

As for doses of the agent for treatment of bladder troubles of the present invention, for example, when a phosphate buffered physiological saline containing 0.2–0.6% by weigh of sodium hyaluronate having an endotoxin content of 0.03 EU (endotoxin unit)/10 mg or less, sulfur content of 0.01% or less as determined by coulometric titration, iron content of 20 ppm or less, protein content of 0.1% or less, and weight average molecular weight of 600,000–1,200,000 is used as the agent for treatment of bladder troubles, it may be administered once to seven times a week at a dose of 50 ml per single administration.

The agent for treatment of bladder troubles of the present invention can be widely used for bladder troubles in generic sense so long as the troubles are those whose symptoms can be improved by dilatation of vesical mucosa epithelium and/or healing of vesical mucosa. It is particularly effective for treatment of non-bacterial intractable bladder troubles, for example, hemorrhagic cystitis such as radiation cystitis caused by radiotherapy of uterine cancer, rectal cancer, cystocarcinoma, prostate cancer and the like and drug cystitis caused by chemotherapeutants for treatment of malignancy, e.g., cyclophosphamide, mitomycin, platinum chelates such as cisplatin, methotrexate, bleomycin hydrochloride, and bleomycin sulfate, stimulation therapy agents for treatment of rheumatism such as auranofin; interstitial cystitis; eosinophilic cystitis; neurogenic increased urinary frequency, and the like.

Because the agent for treatment of bladder troubles of the present invention has action for promoting vesical mucosa epithelium dilatation, and heals vesical mucosa damaged by cystitis, thereby exhibiting excellent action for inhibiting fibrillation of bladder, bladder troubles can be effectively treated by the agent. Further, because the agent for treatment of bladder troubles of the present invention does not show anti-thrombogenic activity, it can be used without causing adverse drug reactions such as becoming easy to bleed.

As for safety of hyaluronic acid (drug toxicity, and noninflammability), many experiments have been already performed, and the safety has been confirmed.

The agent for treatment of bladder troubles of the present invention has an action for promoting vesical mucosa epithelium dilatation and an action for healing vesical mucosa, prevents progress of fibrillation of bladder, and recovers expansion function of bladder, and therefore it exhibits excellent curative effect against bladder troubles.

(3) Kit of the Present Invention

The kit of the present invention comprises a solution containing more than 0.3% by weight and less than 0.6% by weight of hyaluronic acid and/or a pharmaceutically acceptable salt thereof, and a container which contains the solution and is adapted for administration of the solution to the inside of a bladder.

The container preferably comprises a flexible catheter passable through a urethra, and a body which stores the solution.

Preferably, the body is entirely made of a flexible material.

The body preferably has a structure which can be externally pressurized when the solution is infused into the urethra. The structure is preferably adapted for pressurizing by a grip.

EXAMPLES

The present invention will be further explained more specifically with reference to the following examples.

Examples 1-3

Agents for treatment of bladder troubles were prepared by dissolving sodium hyaluronate having an endotoxin content of 0.006 EU (endotoxin unit)/10 ml, sulfur content of 0.005% as determined by coulometric titration, iron content of 4.6 ppm, protein content of 0.01%, and weight average molecular weight of 890,000 in PBS (phosphate buffered saline) so that the content of the sodium hyaluronate should be 0.1% by weight for Example 1, 0.2% by weight for Example 2, and 0.4% by weight for Example 3. The agents for treatment of bladder troubles provided in Examples 1–3 are hereinafter referred to as agent for treatment of bladder troubles 1, agent for treatment of bladder troubles 2, and agent for treatment of bladder troubles 3, respectively. Limiting viscosity and relative osmotic pressure of the agents for treatment of bladder troubles provided above and PBS were measured. The results are shown in Table 1.

TABLE 1

| | Composition | Limiting viscosity (dl/g) | Relative osmotic pressure |
|---|---|---|---|
| Example 1 | 0.1% Sodium hyaluronate solution in PBS | 15.7 | 1.04 |
| Example 2 | 0.2% Sodium hyaluronate solution in PBS | 15.7 | 1.04 |
| Example 3 | 0.4% Sodium hyaluronate solution in PBS | 15.8 | 1.06 |
| Control | PBS | — | 1.03 |

<Evaluation of Agents for Treatment of Bladder Troubles of the Present Invention Using Acetic Acid-Induced Rabbit Cystitis Model>

Using the agents for treatment of bladder troubles provided in Examples 1-3, action for promoting vesical mucosa epithelium dilatation or action for healing vesical mucosa of the agents for treatment of bladder troubles of the present invention for the 5% acetic acid-induced rabbit cystitis model were examined, and the results were used as evaluation of bladder trouble curative effect.

1) Preparation of Rabbit Cystitis Model

Eleven rabbit cystitis models for each of the above-provided agents for treatment of bladder troubles 1–3 and control (PBS), 44 rabbits in total, were prepared as follows.

Forty four 12–14 week-old JW male rabbits (CONV.) having a body weight of about 3 kg were intravenously introduced with 5 mg/kg of ketamine and 2 mg/kg of xylazine for general anesthesia. Then, a bladder catheter provided with a balloon of 8 Fr size was inserted into bladders, and residual urine in the bladders was drained using a 20 ml infusion pipe. After the drainage of residual urine, inside of the bladders was washed twice with 20 ml of physiological saline. Then, 10 ml of solution comprising acetic acid (Wako Pure Chemical Industries, Co., Ltd.) diluted with distilled water to a concentration of 5% was introduced into the bladders, and retained for 10 minutes to induce cystitis. After the cystitis induction the acetic acid was drained, and intravesical irrigation was performed with 20 ml of physiological saline.

2) Administration Test of Agents for Treatment of Bladder Troubles

Each of the agents for treatment of bladder troubles 1–3 provided in the above examples and PBS for control was introduced into bladders of rabbits of each group induced with cystitis as described above using a catheter once a day in an amount of 40 ml immediately after the cystitis induction, 20 ml on day 1 after the induction, and 10 ml on day 2 to day 6, and the introduced agents or PBS were retained for 10 minutes for each time. After pulling out the catheter after the retention of ten minutes, test solution or PBS remained in bladders were drained ad libitum.

3) Evaluation of Action for Promoting Vesical Mucosa Epithelium Dilatation or Action for Healing Vesical Mucosa (Cystitis Curative Effect)

In the rabbits administered with the agents for treatment of bladder troubles 1–3 obtained in the examples as described above or PBS alone, the action for promoting vesical mucosa epithelium dilatation or the action for healing vesical mucosa (cystitis curative effect) were evaluated on day 7 after the cystitis induction based on the following evaluation items. Ten rabbits were used for the evaluation of the evaluation items (a)-(e), one remaining rabbit was used for the evaluation of the item (f).

(a) Determination of Amount of Trypan Blue Injectable to Inside of Bladder (Bladder Capacity)

On day 7 after the cystitis induction, residual urine in bladders of rabbits was drained, and 20 ml of preliminarily prepared 0.5% aqueous solution of trypan blue (Wako Pure Chemicals Industries, Co., Ltd.) was gradually introduced into the bladders of rabbits. When the solution overflowed from the top of penises, injection limit amount was calculated from amount of the remained trypan blue aqueous solution, and that was recorded as bladder capacity.

From the results of the above determination, mean and standard deviation of bladder capacity of 10 animals in each administration group were calculated and represented as a graph (FIG. 1). The mean values of bladder capacity were 8 ml for the control group, 17.8 ml for the agent for treatment of bladder troubles 1 administration group, 16.3 ml for the agent for treatment of bladder troubles 2 administration group, and 17 ml for the agent for treatment of bladder troubles 3 administration group. The indication "**" in FIG. 1 means that the differences between the results of the test groups and the control group is significant with $p \leq 0.01$ when linearity of the measured data was confirmed by a re-sampling method (Multitest Procedure), and the difference of the mean values was tested by Dunnett multiple comparison test.

From the mean values mentioned above and FIG. 1, it is clear that bladder capacity of any of the rabbits of 5% acetic acid-induced rabbit cystitis model administered with the agents for treatment of bladder troubles 1–3 obtained in the above examples was significantly larger than bladder capacity of the rabbits administered with PBS. This difference of bladder capacity is considered to be caused by the fact that, in the control group, severe inflammation was caused after excoriation of vesical mucosa epithelium by acetic acid, and the vesical proper muscle coat caused fibrillation on day 7, thereby expansion became very difficult, whereas, in the agents for treatment of bladder troubles 1–3 administration groups, the fibrillation of vesical proper muscle coat was inhibited by the administration of the therapeutic agents, thereby bladder expansion function was improved.

(b) Photography of Trypan Blue Adhesion to Damaged Area of Bladder and Determination of Bladder Trouble Area Ratio The 0.5% trypan blue aqueous solution was introduced into bladders of the rabbits to the injection limit amounts as described above, and retained for 5 minutes. Then, rabbits were killed by bleeding, and the bladders were excised. The excised bladders were dissected along extracystic blood vessels, and washed by floating them in physiological saline.

After the washing, the bladders were opened, and fixed with pins so that intravesical walls should be upside, and each bladder was photographed as a whole at the same magnification (FIGS. 2–5). FIGS. are representative photographs among photographs of dissected bladders of 10 animals representing trypan blue adhesion to vesical mucosa, with FIG. 2 being for the control group, FIG. 3 for the agent for treatment of bladder troubles 1 administration group, FIG. 4 for the agent for treatment of bladder troubles 2 administration group, and FIG. 5 for the agent for treatment of bladder troubles 3 administration group.

It has known that trypan blue, an acidic living tissue staining agent, can readily stain damaged mucosa From the aforementioned photographs, it has been revealed that the trypan blue adhered area of vesical mucosa, i.e., size of the damaged area of vesical mucosa is largest in the control, where trypan blue adhered to almost all of the vesical inner surface, and it becomes smaller in the order of the agent for treatment of bladder troubles 1 administration group, where trypan blue adhered area was about half of that observed in the control group, the agent for treatment of bladder troubles 2 administration group, and the agent for treatment of bladder troubles 3 administration group.

From the aforementioned photographs representing trypan blue adhesion to the vesical mucosa, total intravesical areas and the damaged areas adhered with trypan blue, which were stained blue, were also determined, and bladder trouble area ratio (%) was calculated according to the following equation:

Bladder trouble area ratio (%)=(trypan blue adhered area/total intravesical area)×100

Figure 6:
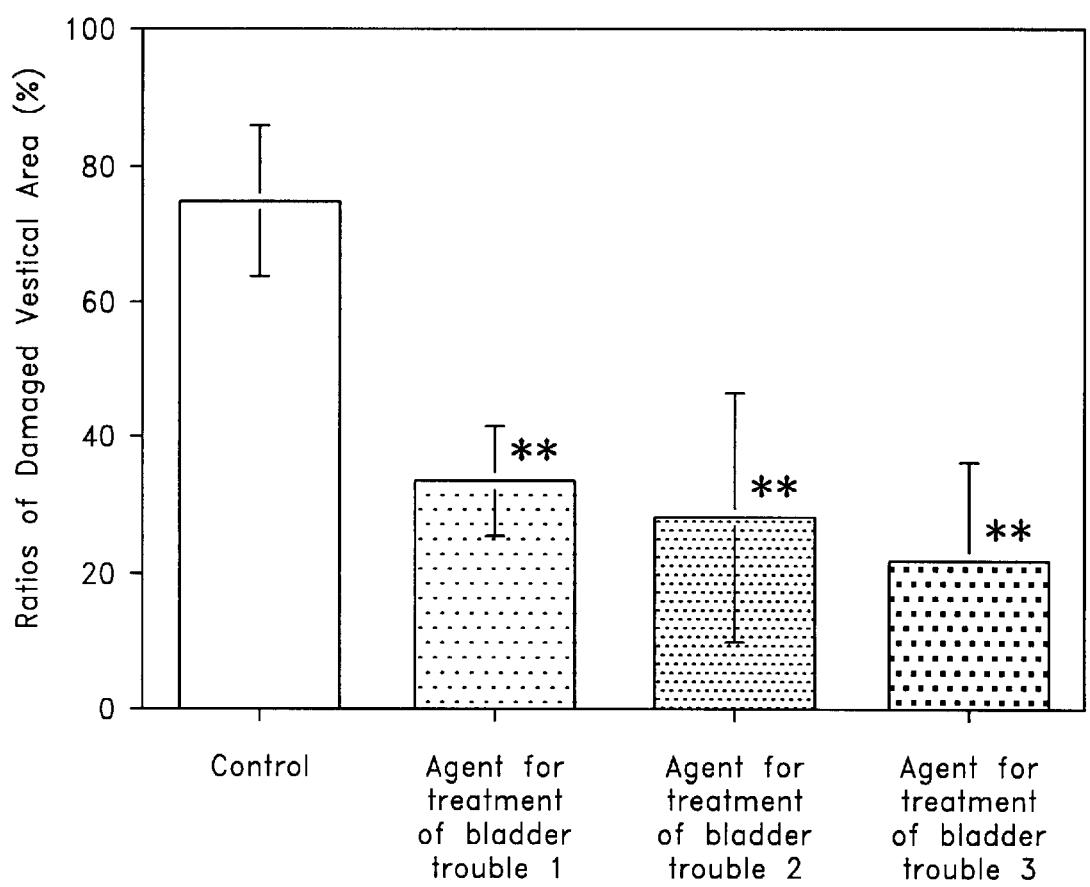
FIG. 6 is a graph representing ratios of damaged vesical area (trypan blue adhered area/total intravesical area) in 5% acetic acid-induced rabbit cystitis models for control and groups administered with agents for treatment of bladder troubles.

From the results of the above calculation, mean and standard deviation of bladder trouble area ratio of 10 animals in each administration group were calculated, and represented as a graph (FIG. 6). The mean values of bladder trouble area ratio were 74.77% for the control group, 33.2% for the agent for treatment of bladder troubles 1 administration group, 28.15% for the agent for treatment of bladder troubles 2 administration group, and 21.84% for the agent for treatment of bladder troubles 3 administration group. The indication "**" in FIG. 6 means that the differences between the results of the test groups and the control group is significant with $p \leq 0.01$ when linearity of the measured data was confirmed by a re-sampling method (Multitest Procedure), and the difference of the mean values was tested by Dunnett multiple comparison test.

From the mean values mentioned above and FIG. 6, it is clear that bladder trouble area ratio of any of the rabbits of 5% acetic acid-induced rabbit cystitis model administered with the agents for treatment of bladder troubles 1–3 obtained in the above examples was significantly smaller than bladder trouble area ratio of the rabbits administered with PBS. Further, significant linearity between the bladder trouble area ratio and the amount of sodium hyaluronate contained in the agents for treatment of bladder troubles administered, i.e., dose-dependency, was observed. These results are considered to show that, by administering the agents for treatment of bladder troubles containing sodium hyaluronate in the amounts mentioned above to the 5% acetic acid-induced rabbit cystitis models, dilatation of vesical mucosa epithelium may be promoted, and vesical mucosa damaged by acetic acid may be healed.

(c) Determination of Bladder Dry Weight

After the photography in the above (b), the bladders were individually lyophilized, macerated, and weighed.

Figure 7:
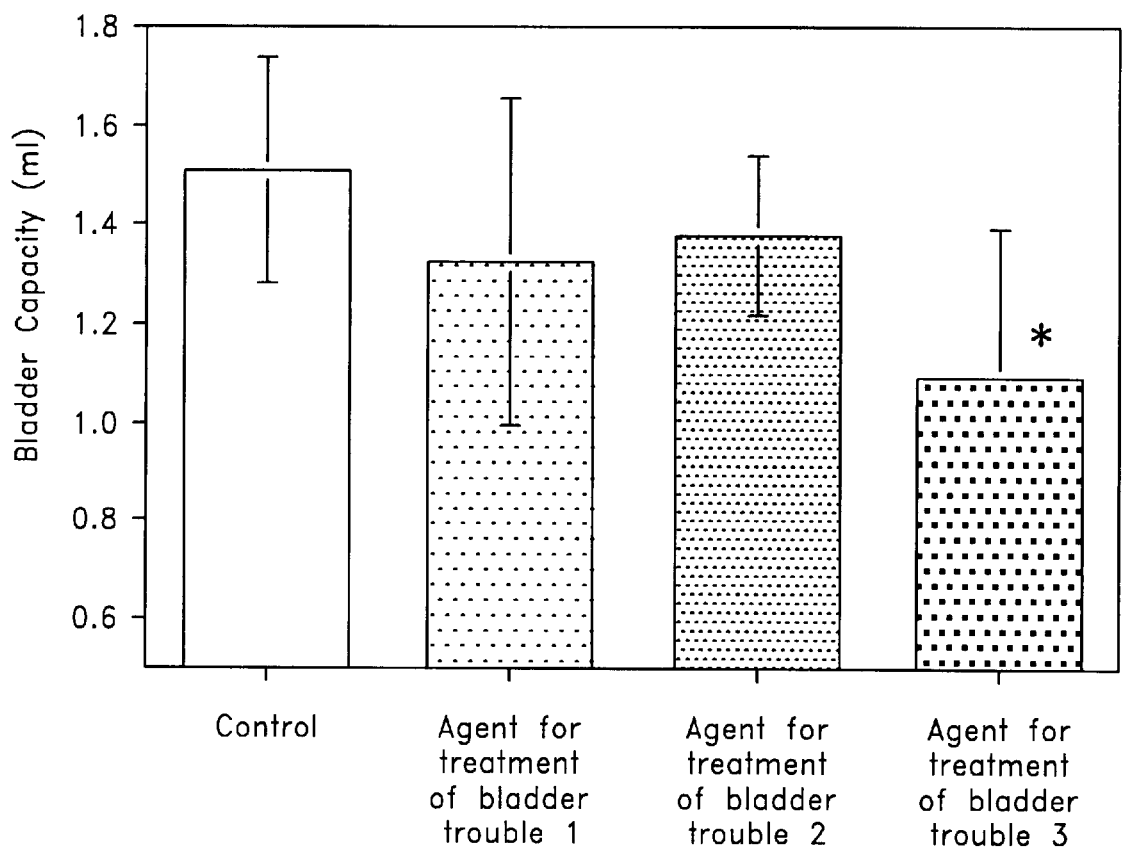
FIG. 7 is a graph representing bladder dry weight in 5% acetic acid-induced rabbit cystitis models for control and groups administered with agents for treatment of bladder troubles.

From the results of the weighing, mean and standard deviation of bladder dry weight of 10 animals in each administration group were calculated and represented as a graph (FIG. 7). The indication "**" in FIG. 7 means that the differences between the results of the test groups and the control group is significant with $0.01 \leq p \leq 0.05$ when linearity of the measured data was confirmed by a re-sampling method (Multitest Procedure), and the difference of the mean values was tested by Dunnett multiple comparison test.

From FIG. 7, it is clear that bladder dry weight of any of the rabbits of 5% acetic acid-induced rabbit cystitis model administered with the agents for treatment of bladder troubles 1–3 obtained ion the above examples was smaller than bladder dry weight of the rabbits administered with PBS.

(d) Determination of Amount of Trypan Blue Adhesion to Damaged Area of Bladders

The bladders after the above weighing were digested with 0.25% actinase, a part of the digest was filtered to afford supernatants, and absorbance of these supernatants at 582 nm was measured. From the obtained values, amounts of trypan blue adhesion were calculated.

Figure 8:
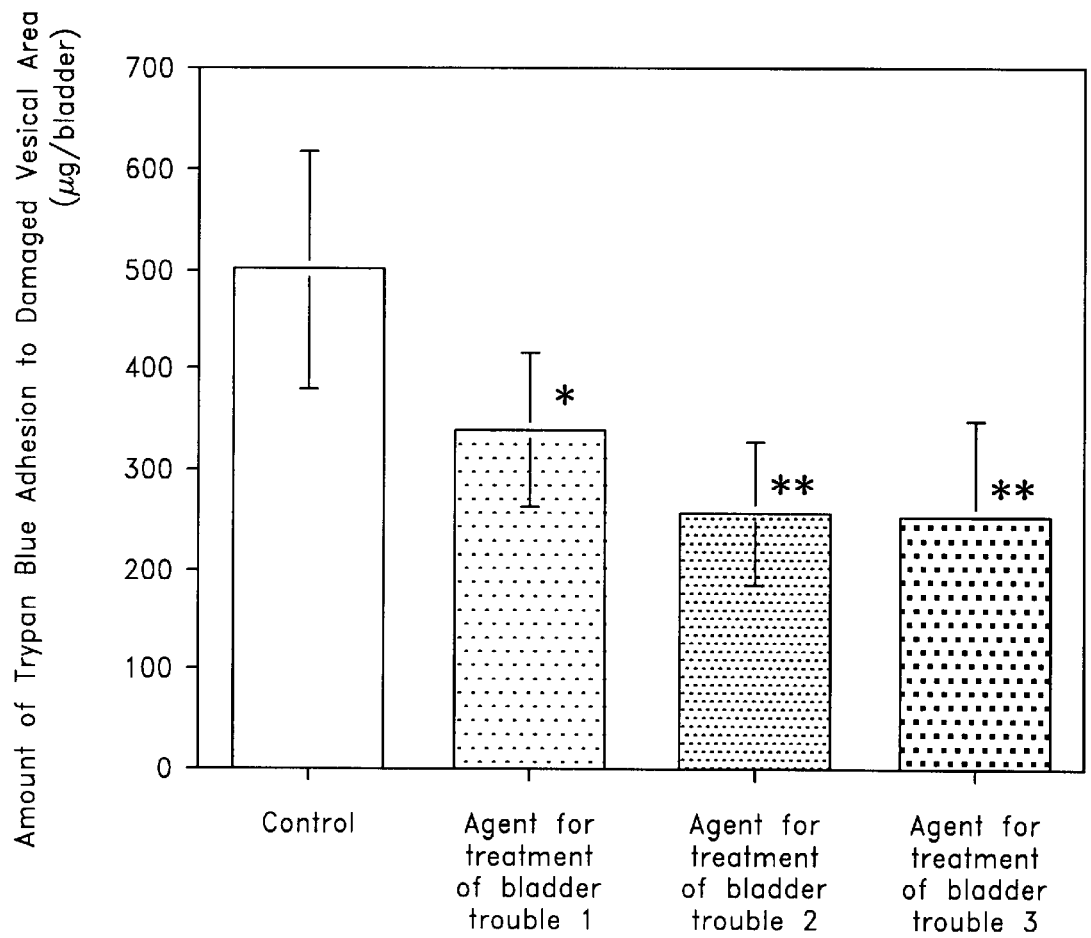
FIG. 8 is a graph representing amount of trypan blue adhesion to damaged vesical area in 5% acetic acid-induced rabbit cystitis models for control and groups administered with agents for treatment of bladder troubles.

From the results of the above determination, mean and standard deviation of amounts of trypan blue adhesion of 10 animals in each administration group were calculated and represented as a graph (FIG. 8). The mean values of amount of trypan blue adhesion were 507 μg/bladder for the control group, 341μg/bladder for the agent for treatment of bladder troubles 1 administration group, 264 μg/bladder for the agent for treatment of bladder troubles 2 administration group, and 265 μg/bladder for the agent for treatment of bladder troubles 3 administration group. The indications "*" and "**" in FIG. 8 mean that the differences between the results of the test groups and the control group are significant with $0.01 \leq p \leq 0.05$ and $p \leq 0.01$, respectively, when linearity of the measured data was confirmed by a re-sampling method (Multitest Procedure), and the difference of the mean values was tested by Dunnett multiple comparison test.

From the mean values mentioned above and FIG. 8, it is clear that amount of trypan blue adhesion of any of the rabbits of 5% acetic acid-induced rabbit cystitis model administered with the agents for treatment of bladder troubles 1–3 was significantly smaller than amount of trypan blue adhesion of the rabbits administered with PBS. Further, significant linearity between the bladder trouble area ratio and the amount of sodium hyaluronate contained in the agent for treatment of bladder troubles administered, i.e., dose-dependency, was observed. These results are considered to show that, by administering the agents for treatment of bladder troubles containing sodium hyaluronate in the amounts mentioned above to the 5% acetic acid-induced rabbit cystitis models, dilatation of vesical mucosa epithelium can be promoted, and vesical mucosa damaged by acetic acid can be healed.

(e) Quantitative Assay of Intravesical Hydroxyproline (Collagen)

A part of the actinase digest obtained above was hydrolyzed with hydrochloric acid. Amount of hydroxyproline formed by the hydrolysis (amount of collagen) was assayed by a conventional manner, and amount of intravesical hydroxyproline (amount of collagen) was calculated.

Figure 9:
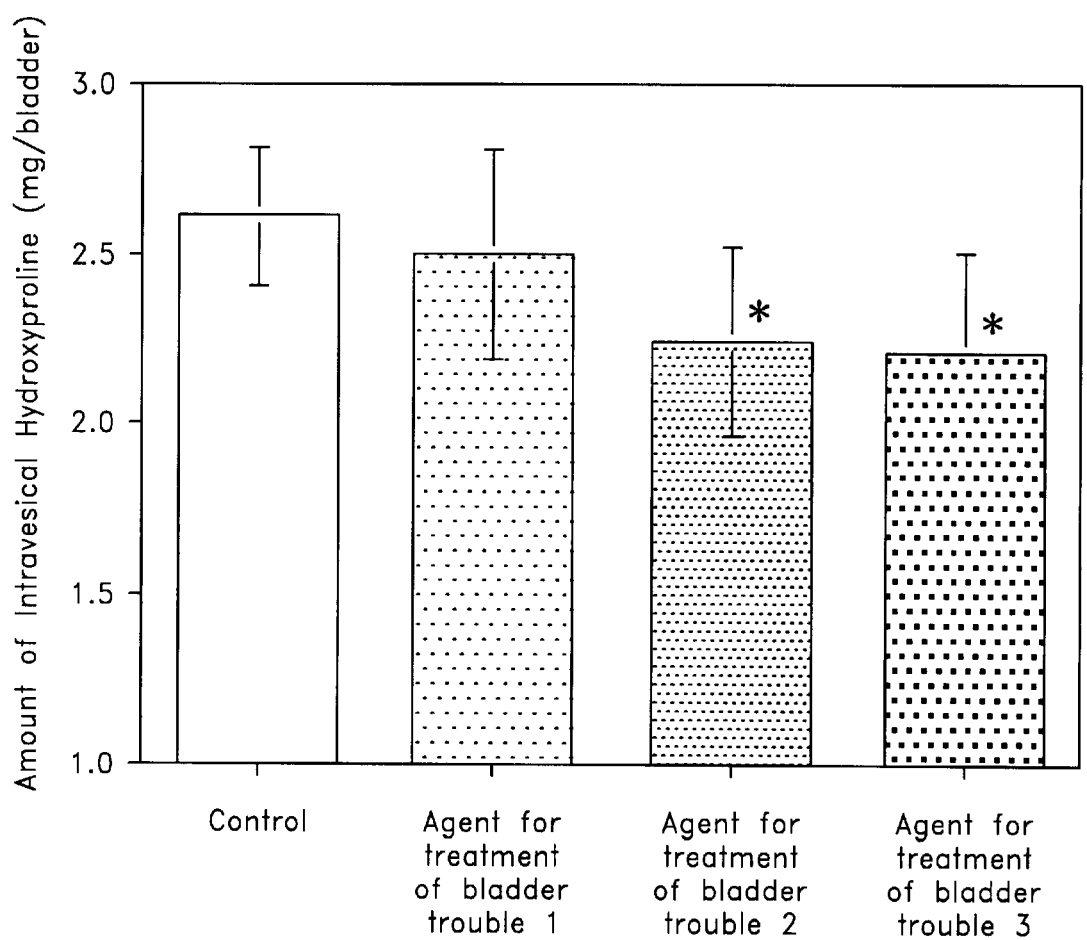
FIG. 9 is a graph representing amount of intravesical hydroxyproline (collagen) in 5% acetic acid-induced rabbit cystitis models for control and groups administered with agents for treatment of bladder troubles.

From the results of the above assay, mean and standard deviation of amount of hydroxyproline of 10 animals in each administration group were calculated and represented as a graph (FIG. 9). The indication "*" in FIG. 9 means that the differences between the results of the test groups and the control group are significant with of $0.01 \leq p \leq 0.05$, when linearity of the data was confirmed by a re-sampling method (Multitest Procedure), and the difference of the mean values was tested by Dunnett multiple comparison test.

From FIG. 9, it is clear that amount of intravesical hydroxyproline of any of the rabbits of acetic acid-induced rabbit cystitis model administered with the agents for treatment of bladder troubles 1–3 was smaller than amount of intravesical hydroxyproline of the rabbits administered with PBS. These results are considered to show that, by administering the agents for treatment of bladder troubles containing sodium hyaluronate in the amounts mentioned above to the 5% acetic acid-induced rabbit cystitis models, fibrillation of bladders can be prevented.

(f) Histopathological Examination

On day 7 after the cystitis induction, after remained urine in bladders of rabbits was drained, 10 ml of preliminarily prepared 10% phosphate buffered formalin solution was introduced into the bladders of rabbits, then the rabbits were killed by bleeding, and the bladders were removed. The removed bladders were fixed by placing them in 10% phosphate buffered formalin solution when they were still in the inflated state, and histopathological examination was performed by hematoxylin-eosin staining and Azan staining methods.

Microphotographs (25 magnifications) of vesical tissues stained with hematoxylin-eosin or Azan are shown in FIGS. 10–13. FIG. 10 shows photographs of stained vasical tissue for the control group, FIG. 11 for the agent for treatment of bladder troubles 1 administration group, FIG. 12 for the agent for treatment of bladder troubles 2 administration group, and FIG. 13 for the agent for treatment of bladder troubles 3 administration group. In these figures, (a) indicates photographs of hematoxylin-eosin staining in 25 magnifications, and (b) indicates photographs of Azan staining in 25 magnifications.

Figure 10A:
FIG. 10 shows photographs of stained bladder tissue of 5% acetic acid-induced rabbit cystitis model for control. (a) is a photograph of hematoxylin-eosin stained tissue in 25 magnifications, and (b) is a photograph of Azan stained tissue in 25 magnifications.
Figure 10B:

FIG. 10(a) indicates that, in the bladder of the control group, no vesical mucosa epithelium was recognized for total inner surface of the bladder, massive necrotic tissues projecting into the cavity were observed, amorphous matters were observed on the surfaces of the massive necrotic tissues, and severe cellular infiltration was seen in the lining. FIG. 10(b) indicates that, in the bladder of the control group, formation of collagen fibers, which are stained blue with Azan, was observed in the total inner surface of the bladder, and an image which may be called as bladder induration was provided.

Figure 11A:
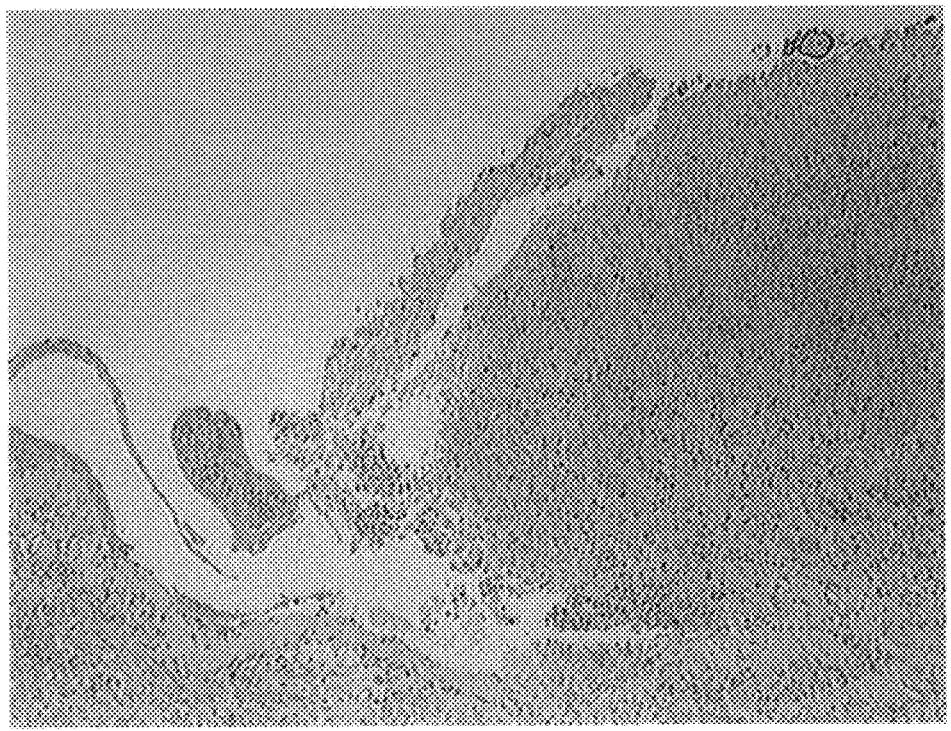
FIG. 11 shows photographs of stained bladder tissue of 5% acetic acid-induced rabbit cystitis model for a group administered with agent for treatment of bladder troubles 1. (a) is a photograph of hematoxylin-eosin stained tissue in 25 magnifications, and (b) is a photograph of Azan stained tissue in 25 magnifications.
Figure 11B:
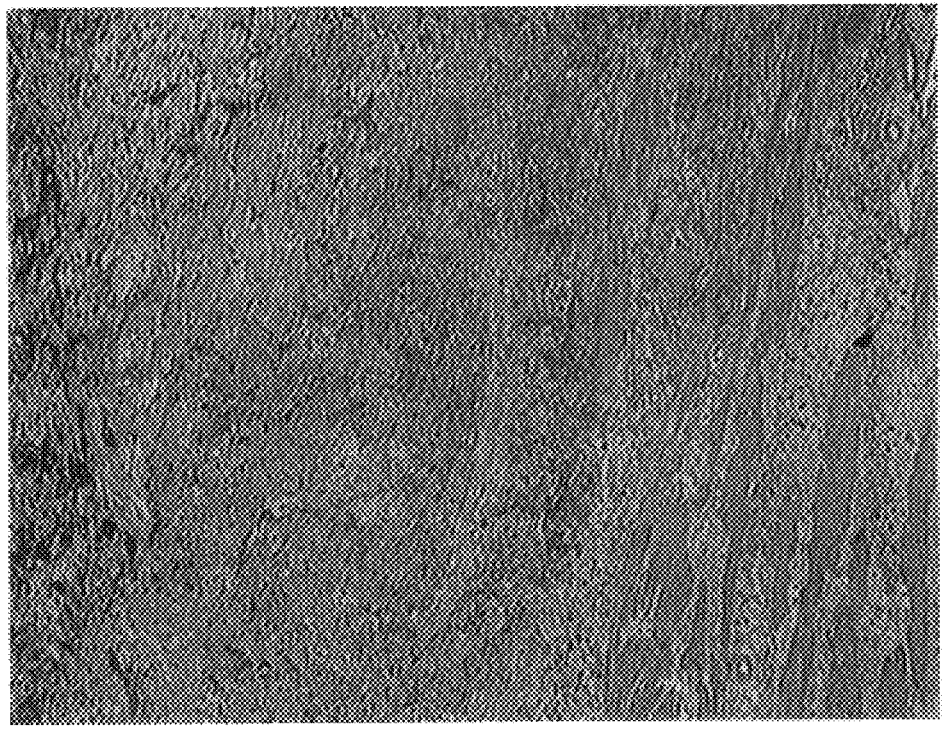

FIG. 11(a) indicates that, in the bladder of the agent for treatment of bladder troubles 1 administration group, while massive necrotic tissues were observed like in the control group, formation of vesical mucosa epithelium not seen in the control group was recognized, and, though mucosa epithelium cell alignment was irregular, necrotic image was not observed. FIG. 11 (b) indicates that, in the bladder of the agent for treatment of bladder troubles 1 administration group, an image that can be called as bladder induration was seen for the apparent granulation region like the control group.

Figure 12A:
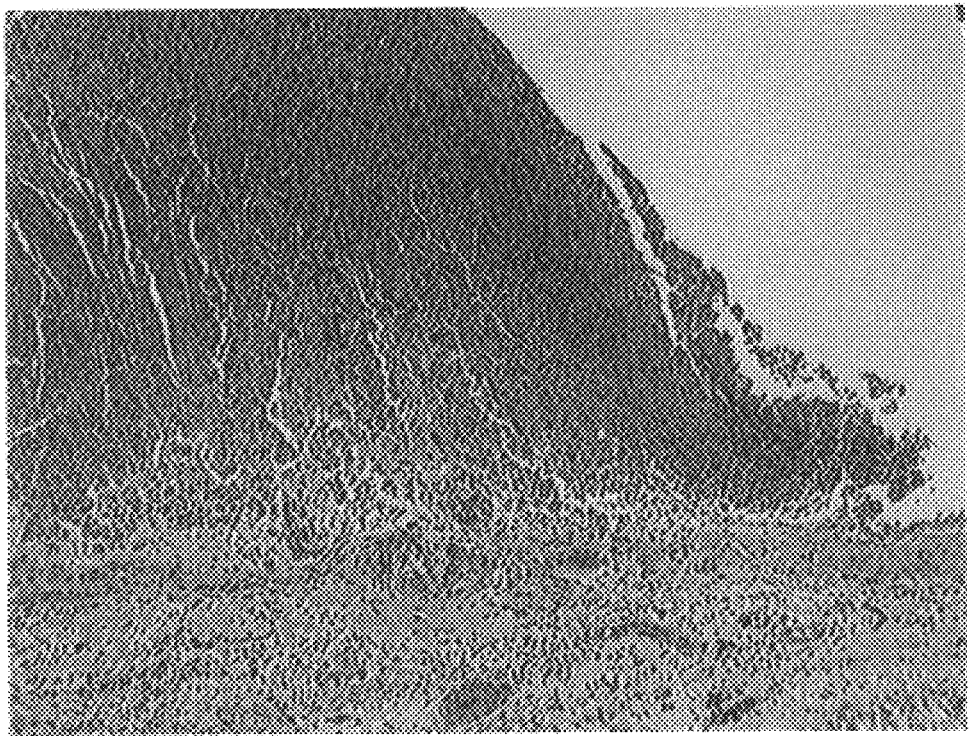
FIG. 12 shows photographs of stained bladder tissue of 5% acetic acid-induced rabbit cystitis model for a group administered with agent for treatment of bladder troubles 2. (a) is a photograph of hematoxylin-eosin stained tissue in 25 magnifications, and (b) is a photograph of Azan stained tissue in 25 magnifications.
Figure 12B:
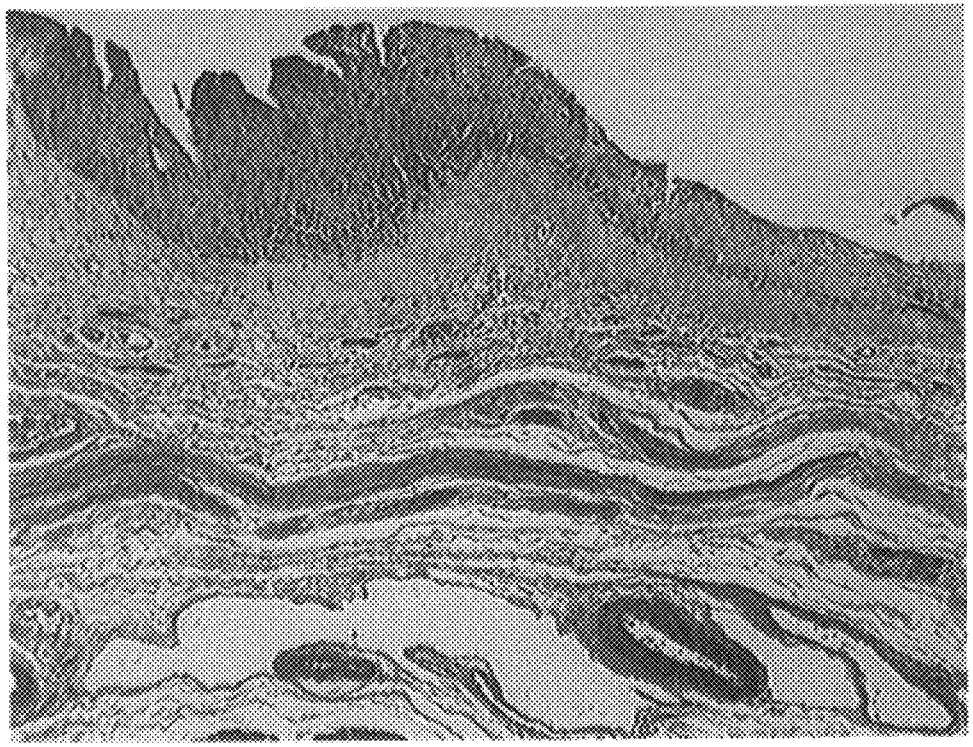

FIG. 12 (a) indicates that, in the bladder of the agent for treatment of bladder troubles 2 administration group, massive necrotic tissues projecting into the bladder were observed in a wider range compared with the agent for treatment of bladder troubles 1 administration group. However, FIG. 12 (b) indicates that, in the bladder of the agent for treatment of bladder troubles 2 administration group, though a bladder induration image was observed, condition of mucosal epithelium was substantially normal.

Figure 13A:
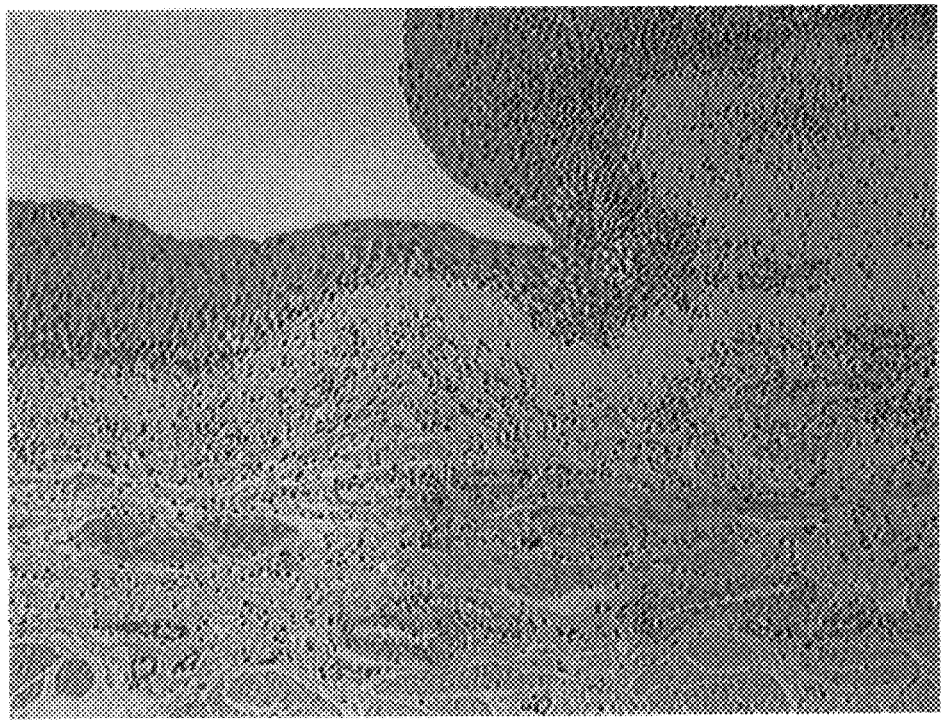
FIG. 13 shows photographs of stained bladder tissue of 5% acetic acid-induced rabbit cystitis model for a group administered with agent for treatment of bladder troubles 3. (a) is a photograph of hematoxylin-eosin stained tissue in 25 magnifications, and (b) is a photograph of Azan stained tissue in 25 magnifications.
Figure 13B:
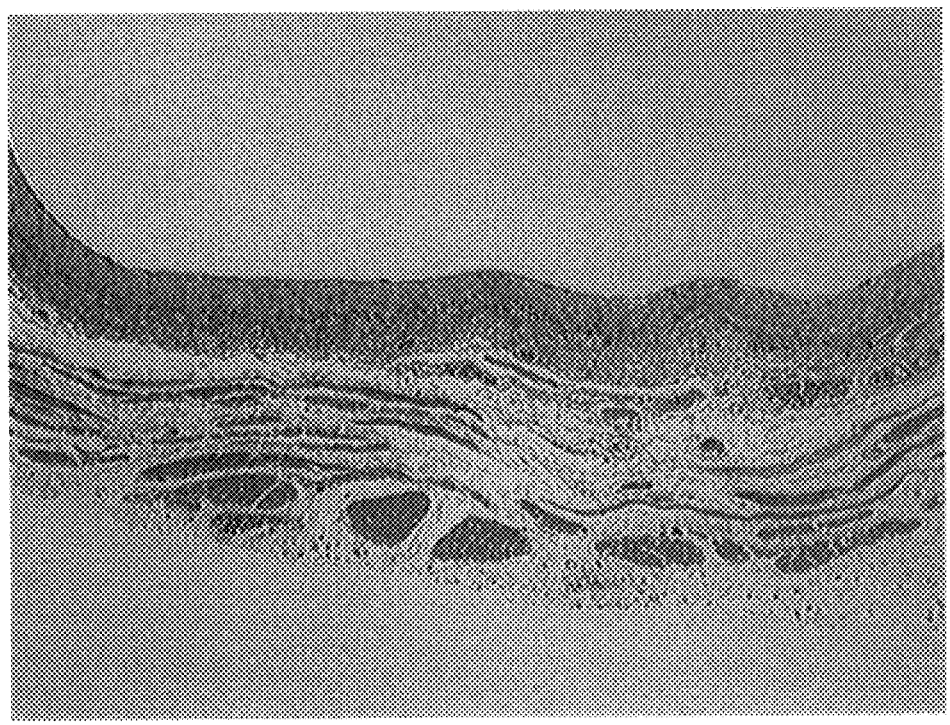

FIG. 13 (a) indicates that, in the bladder of the agent for treatment of bladder troubles 3 administration group, no massive necrotic tissue projecting into the bladder was observed at all. FIG. 13 (b) indicates that, in the bladder of the agent for treatment of bladder troubles 3 administration group, a bladder induration image was not observed.

In summary, any of the bladders of the rabbits of the to 5% acetic acid-induced rabbit cystitis models after administered with the agents for treatment of bladder troubles 1–3 provided in the above examples exhibited smaller histopathological difference relative to bladders of normal rabbits compared with the bladders of the rabbits after administered with PBS. Furthermore, in the agent for treatment of bladder troubles 3 administration group where the agent contained 0.4% by weight of sodium hyaluronate, markedly good results were provided, i.e., no massive necrotic tissue was observed. The results of the histopathological examination are considered to support the results of the determination of bladder capacity, bladder dry weight, trypan blue adhesion area, amount of trypan blue adhesion, and amount of hydroxyproline (amount of collagen).

As seen from the results mentioned above, bladder capacity, trypan blue adhesion area, amount of trypan blue adhesion, amount of hydroxyproline, and bladder weight could be improved, and healing and improving effects of vesical mucosa due to vesical mucosa epithelium dilatation were observed in the histopathological examination when the agents for treatment of bladder troubles 1–3 provided in the above examples were administered to 5% acetic acid-induced rabbit cystitis models. Therefore, it can be considered that the agent for treatment of bladder troubles of the present invention can provide effective therapy for bladder troubles by promoting vesical mucosa epithelium dilatation, and healing vesical mucosa, thereby inhibiting fibrillation.

Example 4

Methods:
(1) Test Solution

Sodium hyaluronate (HMT) solutions having concentrations shown below were used. Solvent was phosphate buffered saline (PBS). The weight average molecular weight of the used HMT is 840,000.
(a) 0.20% by weight
(b) 0.30% by weight
(c) 0.35% by weight
(d) 0.40% by weight
(e) 0.45% by weight
(f) 0.60% by weight As controls, PBS was used.

(2) Grouping of Animals 147 of SD females rats (about 10 week-old, body weight: 200 to 260 g) were divided into the following 8 groups.

| Administration group | Number of animals |
| --- | --- |
| PBS | 20 |
| 0.20% HMT | 20 |
| 0.30% HMT | 20 |
| 0.35% HMT | 20 |
| 0.40% HMT | 20 |
| 0.45% HMT | 20 |
| 0.60% HMT | 20 |
| Untreated (Normal) | 7 |

(3) Preparation of Rat Cystitis Model

To SD female rats, Nembutal (Dainippon Pharmaceutical) was intraperitoneally administered for general anesthesia. A 24-G catheter (Terumo) was inserted into each bladder, and residual urine in the bladder was drained by using a 2.5-ml injection syringe with a 27-G needle. After that, inside of the bladder was washed thrice with 1 ml of physiological saline. Then, 500 µl of 5% aqueous acetic acid solution was introduced into the bladder, and retained for 10 minutes to induce cystitis. After that, the acetic acid solution was drained, and intravesical irrigation with 1 ml of physiological saline was performed thrice.

(4) Administration Test of Sodium Hyaluronate

Administration was performed once a day for 4 days (4 times in total).

First administration: Each of the test solutions was introduced into bladders of the cystitis-induced rats of each group by using a catheter immediately after the cystitis induction. The introduction was performed in an introducible amount until the test solution flows backward from urethra, and the test solution was retained for 10 minutes. After the retention of 10 minutes, the catheter was pulled out, and the test solution in the bladder was drained ad libitum.

Second to forth administrations: The administration was performed under ether anesthesia. Residual urine in the bladder was drained by using a catheter. Inside of the bladder was washed thrice with physiological saline in the introducible amount. The test solution was administered by using a catheter in the introducible amount as in the first administration.

(5) Determination of Bladder Capacity

On day 4 after the cystitis induction, rats were sacrificed by administration of an excess amount of Nembutal (Dainippon Pharmaceutical). Abdomen was incised to expose the bladder. After drain of residual urine in the bladder, a catheter was inserted into the urethra, and physiological saline was gradually introduced into the bladder at a pressure of 50 cm $H_2O$. The introduction was stopped when backward flow of physiological saline from the urethra was observed, and then the urethra was ligated. The bladder was extracted and weighed. After physiological saline in the bladder was drained and liquid was wiped out, the bladder was weighed. The bladder volume was calculated by deducting the weight after drain of physiological saline from the weight before the drain.

(6) Statical Analysis

Statical analysis of the results was performed with statics assistance system SAS (SAS Institute Japan). An average and a standard deviation of the bladder volume were calculated and the difference of the average of each HMT group from the PBS group as a control was tested by Dunnett multiple comparison test. $p<0.05$ was considered to be significant.

Figure 14:
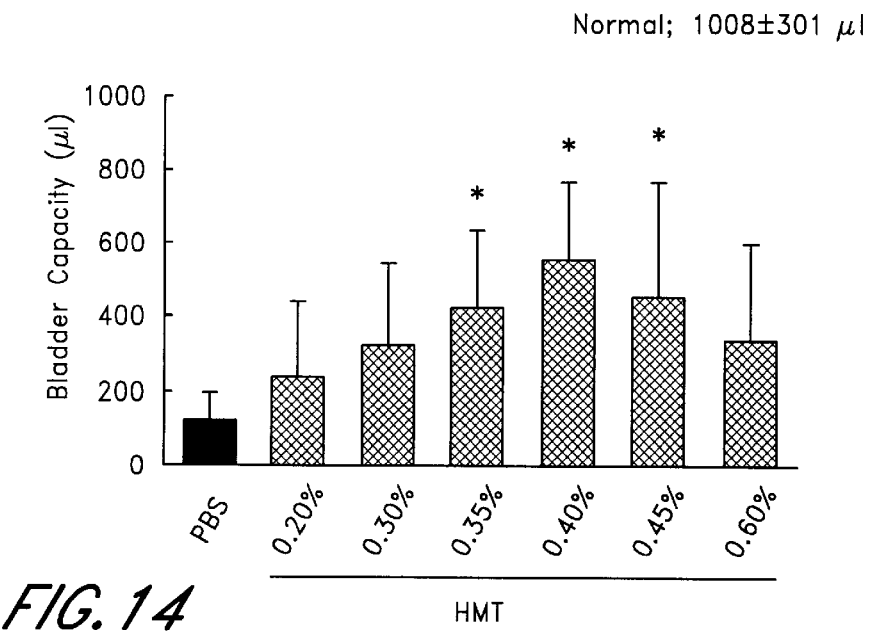
FIG. 14 shows results of treatment of cystitis with sodium hyaluronate solutions in rat cystitis model.

Results:

The results are shown in FIG. 14. In the PBS group, three animals died in the administration period; and four animals were excluded from the analysis because severe adhesion between bladder and another internal organ was observed when the animal was dissected. In the 0.20% HMT group, two animals died in the administration period; and one animal was excluded from the analysis because severe adhesion between bladder and another internal organ was observed when the animal was dissecte. In the 0.30% HMT group, one animal was excluded from the analysis because severe adhesion between bladder and another internal organ was observed when the animal was dissected. In the 0.40% HMT group, two animals died in the administration period; and one animal was excluded from the analysis because bladder was damaged when the animal was dissecte. In the 0.45% HMT group, one animal died in the administration period. In the 0.60% HMT group, one animal died in the administration period. Therefore, numbers of analyzed animals in the administration groups were as follows: PBS: n=13, 0.20% HMT: n=17, 0.30% HMT: n=19, 0.35% HMT: n=20, 0.40% HMT: n=17, 0.45% HMT; n=19, 0.60% HMT: n=19, normal: n=7. In the FIG. 14, * means that it is significant with $p<0.05$ versus PBS (control) by Dunnett multiple comparison test.

From the results shown in the FIG. 14, it was clear that reduction of the bladder capacity of the group in which sodium hyaluronate of 0.35%, 0.40% or 0.45% by weight was administered was significantly suppressed. This indicates that sodium hyaluronate of around 0.4% (more than 0.3 to less than 0.6%) by weight (especially, around 0.35 to around 0.45% by weight) is markedly effective.

Example 5

Methods:

(1) Test Solution

Sodium hyaluronate solutions having concentrations shown below were used. Solvent was phosphate buffered saline (PBS). The weight average molecular weights of the used sodium hyaluronates are shown in parenthesis.

(a) 0.1% by weight (890,000)
(b) 0.2% by weight (890,000)
(c) 0.4% by weight (890,000)
(d) 0.6% by weight (900,000)
(e) 0.8% by weight (910,000)

As a control, PBS was used.

(2) Preparation of Rabbit Cystitis Model

According to the method described in Examples 1–3, 10 ml of 5% aqueous acetic acid solution was introduced into each of bladders of JW male rabbits (12 to 14 week-old, body weight: about 3 kg) and retained for 10 minutes to induce cystitis. Then, intravesical irrigation was performed according to the method described in Examples 1–3.

(3) Administration Test of Sodium Hyaluronate

Each of the test solutions was introduced into bladders of the cystitis-induced rabbits of each group by using a catheter in an amount of 40 ml immediately after the cystitis induction, and then retained for 10 minutes. After the retention of 10 minutes, the catheter was pulled out, and the test solution in the bladder was drained ad libitum.

In the Examples 1–3, because the treatment of bladder once a day totals 7 times after the cystitis induction, the results were not very different among the 0.1%, 0.2% and 0.4% solutions. Therefore, in this experiment, the test was conducted under more severe conditions (treatment of bladder was 1 time).

(4) Determination of Bladder Capacity

On day 7 after the cystitis induction, rabbits were sacrificed and subjected to celiotomy, and bladders were extracted by cutting off bladders around ureter. After drain of residual urine in the bladder, 0.5% aqueous trypan blue solution was gradually introduced into the bladder at the cut-off portion of the bladder, and the introduced amount at a limit of bladder expansion was recorded as the bladder capacity.

In the Examples 1–3, because an upper limit of the introduced amount of the trypan blue solution was 20 ml, the results were not very different among the 0.1%, 0.2% and 0.4% solutions. Therefore, in this experiment, by taking expansion function of bladder into consideration, a more precise bladder capacity (maximum capacity of bladder; volume when the solution is introduced to a limit of bladder expansion) was determined.

Figure 15:
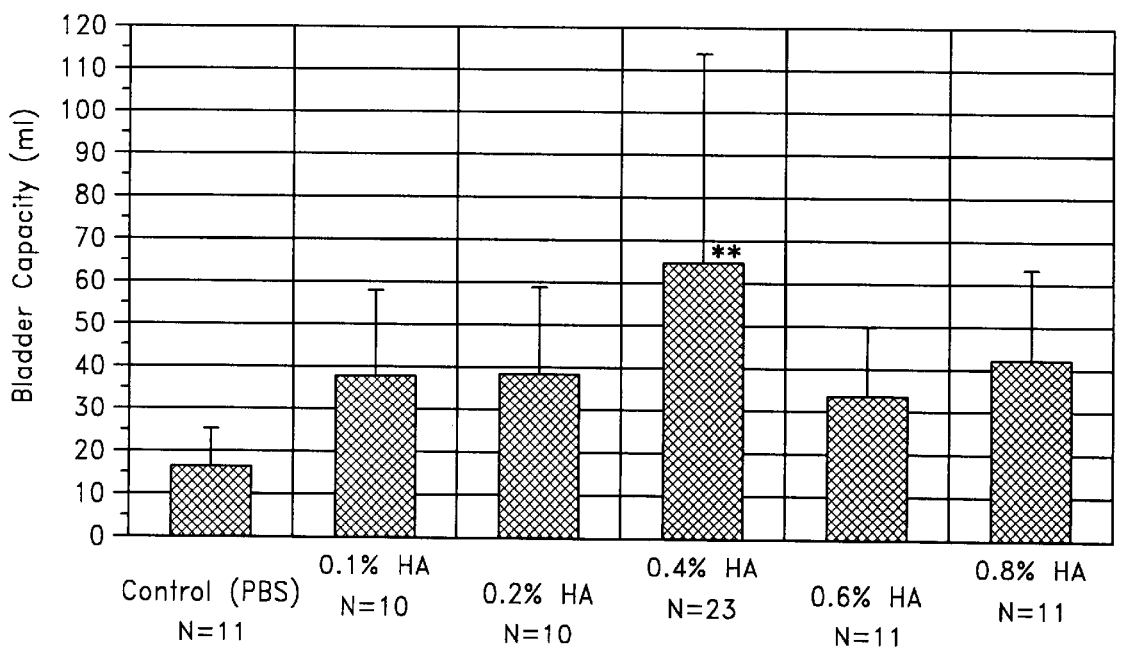
FIG. 15 shows results of treatment of cystitis with sodium hyaluronate solutions in rabbit cystitis model.

Results:

The results are shown in FIG. 15. In the FIG. 15, N is the number of used rabbits. ** means that it is significant with $p<0.01$ (Dunnet multiple comparison test) with respect to the control.

From the results shown in the FIG. 15, it was clear that the bladder capacity of the group in which sodium hyaluronate of 0.4% by weight was administered was larger that those of groups in which sodium hyaluronate of other concentrations were administered. This indicates that administration of sodium hyaluronate of 0.4% by weight remarkably improves expansion function of bladder compared with administration at the other concentrations.

The concentration within a certain range of which center is 0.4% by weight is most effective in rabbits as well as rats.

What is claimed is:

1. A method for promoting vesical mucosa epithelium dilatation and/or healing vesical mucosa of a patient's bladder, comprising: administering to the inside of the patient's bladder a solution comprising hyaluronic acid and/or a pharmaceutically acceptable salt thereof in an amount of 0.35 to 0.45% by weight until promotion of vesical mucosa epithelium dilatation and/or healing vesical mucosa is observed, said patient being in need of promotion of vesical mucosa epithelium dilatation and/ or healing vesical mucosa is observed, said patient being in need of promotion of vesical mucosa epithelium dilatation and/or healing vesical mucosa.

2. A kit comprising a solution containing 0.35 to 0.45% by weight of hyaluronic acid and/or a pharmaceutically acceptable salt thereof, and a container which contains the solution and is adapted for administration of the solution to the inside of a bladder.

3. The kit according to claim 2, wherein the container comprises a flexible catheter passable through a urethra, and a body which stores the solution.

4. The kit according to claim 3, wherein the body is entirely made of a flexible material.

5. The kit according to claim 3, wherein the body has a structure which can be externally pressurized when the solution is infused into the urethra.

6. The kit according to claim 5, wherein the structure is adapted for pressurizing by a grip.

* * * * *

UNITED STATES PATENT AND TRADEMARK OFFICE
CERTIFICATE OF CORRECTION

PATENT NO. : 6,548,487 B2
DATED : April 15, 2003
INVENTOR(S) : Takahashi et al.

It is certified that error appears in the above-identified patent and that said Letters Patent is hereby corrected as shown below:

Column 21,
Line 19, "mucosa is observed, said patient being in need of promotion of vesical mucosa epithelium dilatation and/or healing vesical mucosa is observed, said patient being in need of promotion of vesical mucosa epithelium dilatation and/or healing vesical mucosa" should be changed to -- mucosa is observed, said patient being in need of promotion of vesical mucosa epithelium dilatation and/or healing vesical mucosa. --

Signed and Sealed this

Twenty-third Day of December, 2003

JAMES E. ROGAN
*Director of the United States Patent and Trademark Office*